United States Patent
Arora et al.

(10) Patent No.: US 10,416,092 B2
(45) Date of Patent: Sep. 17, 2019

(54) REMOTE DETECTION OF PLATING ON WAFER HOLDING APPARATUS

(71) Applicant: Lam Research Corporation, Fremont, CA (US)

(72) Inventors: Rajan Arora, Hillsboro, OR (US); Jared Herr, Tigard, OR (US); Jason Daniel Marchetti, Tualatin, OR (US); Steven T. Mayer, Aurora, OR (US); James R. Zibrida, Portland, OR (US)

(73) Assignee: Lam Research Corporation, Fremont, CA (US)

( * ) Notice: Subject to any disclaimer, the term of this patent is extended or adjusted under 35 U.S.C. 154(b) by 2 days.

(21) Appl. No.: 15/638,131

(22) Filed: Jun. 29, 2017

(65) Prior Publication Data

US 2017/0299524 A1 Oct. 19, 2017

Related U.S. Application Data

(63) Continuation-in-part of application No. 14/178,804, filed on Feb. 12, 2014, now Pat. No. 9,746,427.
(Continued)

(51) Int. Cl.
*G01N 21/00* (2006.01)
*G01N 21/95* (2006.01)
(Continued)

(52) U.S. Cl.
CPC ....... *G01N 21/9515* (2013.01); *C25D 17/001* (2013.01); *C25D 17/004* (2013.01);
(Continued)

(58) Field of Classification Search
CPC .......... G01N 21/9501; G01N 27/9046; C25D 21/12; C25D 17/001; C25D 17/06;
(Continued)

(56) References Cited

U.S. PATENT DOCUMENTS 2,773,257 A 12/1956 Craggs et al.
3,225,899 A 12/1965 Lo Presti et al.
(Continued)

FOREIGN PATENT DOCUMENTS

CN 1509348 A 6/2004
CN 1550033 A 11/2004
(Continued)

OTHER PUBLICATIONS

U.S. Notice of Allowance, dated May 30, 2018, issued in U.S. Appl. No. 14/949,681.
(Continued)

*Primary Examiner* — Hoa Q Pham
(74) *Attorney, Agent, or Firm* — Weaver Austin Villeneuve & Sampson LLP

(57) ABSTRACT

Methods and apparatus for detecting the presence or absence of unwanted metal deposits on a substrate holder of an electroplating apparatus are described herein. In various embodiments, a plating sensor is used to detect unwanted metal deposits. The plating sensor may be mounted relatively far away from the area that it measures (e.g., the sensor target area). For instance, the plating sensor may be on one side of the electroplating apparatus (in some cases mounted on a drip shield), and the sensor target area may be on the opposite side of the electroplating apparatus. In this way, the plating sensor can measure across the electroplating apparatus. This placement provides a relatively deep depth of focus for the plating sensor, and provides some physical separation between the plating sensor and the electroplating chemistry. Both of these factors lead to more reliable detection results.

16 Claims, 12 Drawing Sheets

Related U.S. Application Data

(60) Provisional application No. 61/765,502, filed on Feb. 15, 2013.

(51) Int. Cl.
    *C25D 17/06*    (2006.01)
    *C25D 17/00*    (2006.01)
    *C25D 21/12*    (2006.01)
    *G01N 27/90*    (2006.01)
    *G01N 21/94*    (2006.01)

(52) U.S. Cl.
    CPC ............ *C25D 17/06* (2013.01); *C25D 21/12* (2013.01); *G01N 21/94* (2013.01); *G01N 27/9046* (2013.01); *G01N 21/9501* (2013.01)

(58) Field of Classification Search
    CPC .......... C25D 7/12; C25D 17/00; B08B 3/022; B08B 3/041; H01L 21/67769; H01L 21/67766
    USPC .................................. 356/237.1–237.5, 338
    See application file for complete search history.

(56) References Cited

U.S. PATENT DOCUMENTS

| | | | |
|---|---|---|---|
| 3,334,750 A | 8/1967 | Ullman, Jr. |
| 3,430,055 A | 2/1969 | Metzger |
| 3,684,633 A | 8/1972 | Haase |
| 3,716,765 A | 2/1973 | Rueffer et al. |
| 3,724,471 A | 4/1973 | Sitges |
| 4,418,432 A | 12/1983 | Vidal |
| 4,466,864 A | 8/1984 | Bacon et al. |
| 4,569,695 A | 2/1986 | Yamashita et al. |
| 4,654,235 A | 3/1987 | Effenberger et al. |
| 4,924,891 A | 5/1990 | Soubrier et al. |
| 5,000,827 A | 3/1991 | Schuster et al. |
| 5,221,449 A | 6/1993 | Colgan et al. |
| 5,227,041 A | 7/1993 | Brogden et al. |
| 5,281,485 A | 1/1994 | Colgan et al. |
| 5,289,639 A | 3/1994 | Bard et al. |
| 5,311,634 A | 5/1994 | Andros |
| 5,482,611 A | 1/1996 | Helmer et al. |
| 5,519,945 A | 5/1996 | Ahvenniemi et al. |
| 5,723,028 A | 3/1998 | Poris |
| 5,853,559 A | 12/1998 | Tamaki et al. |
| 5,860,361 A | 1/1999 | Nanjyo et al. |
| 5,985,762 A | 11/1999 | Geffken et al. |
| 6,071,388 A | 6/2000 | Uzoh |
| 6,074,544 A | 6/2000 | Reid et al. |
| 6,080,291 A | 6/2000 | Woodruff et al. |
| 6,099,702 A | 8/2000 | Reid et al. |
| 6,108,847 A | 8/2000 | Cueman et al. |
| 6,110,346 A | 8/2000 | Reid et al. |
| 6,124,203 A | 9/2000 | Joo et al. |
| 6,126,798 A | 10/2000 | Reid et al. |
| 6,139,712 A | 10/2000 | Patton et al. |
| 6,156,167 A | 12/2000 | Patton et al. |
| 6,159,354 A | 12/2000 | Contolini et al. |
| 6,162,344 A | 12/2000 | Reid et al. |
| 6,176,985 B1 | 1/2001 | Downes, Jr. et al. |
| 6,179,973 B1 | 1/2001 | Lai et al. |
| 6,179,983 B1 | 1/2001 | Reid et al. |
| 6,193,854 B1 | 2/2001 | Lai et al. |
| 6,217,716 B1 | 4/2001 | Fai Lai |
| 6,221,757 B1 | 4/2001 | Schmidbauer et al. |
| 6,251,238 B1 | 6/2001 | Kaufman et al. |
| 6,251,242 B1 | 6/2001 | Fu et al. |
| 6,261,433 B1 | 7/2001 | Landau |
| 6,267,853 B1 | 7/2001 | Dordi et al. |
| 6,267,860 B1 | 7/2001 | Brodsky |
| 6,270,646 B1 | 8/2001 | Walton et al. |
| 6,274,008 B1 | 8/2001 | Gopalraja et al. |
| 6,277,249 B1 | 8/2001 | Gopalraja et al. |
| 6,303,010 B1 | 10/2001 | Woodruff et al. |
| 6,309,520 B1 | 10/2001 | Woodruff et al. |
| 6,309,981 B1 | 10/2001 | Mayer et al. |
| 6,379,468 B1 | 4/2002 | Chang et al. |
| RE37,749 E | 6/2002 | Poris |
| 6,398,926 B1 | 6/2002 | Mahneke |
| 6,413,388 B1 | 7/2002 | Uzoh et al. |
| 6,436,249 B1 | 8/2002 | Patton et al. |
| 6,517,689 B1 | 2/2003 | Hongo et al. |
| 6,540,899 B2 | 4/2003 | Keigler |
| 6,551,487 B1 | 4/2003 | Reid et al. |
| 6,579,430 B2 | 6/2003 | Davis et al. |
| 6,589,401 B1 | 7/2003 | Patton et al. |
| 6,612,915 B1 | 9/2003 | Uzoh et al. |
| 6,613,214 B2 | 9/2003 | Dordi et al. |
| 6,627,052 B2 | 9/2003 | Fluegel et al. |
| 6,755,946 B1 | 6/2004 | Patton et al. |
| 6,755,954 B2 | 6/2004 | Mayer et al. |
| 6,773,560 B2 | 8/2004 | Pedersen et al. |
| 6,800,187 B1 | 10/2004 | Reid et al. |
| 6,869,510 B2 | 3/2005 | Woodruff et al. |
| 6,908,540 B2 | 6/2005 | Kholodenko |
| 7,033,465 B1 | 4/2006 | Patton et al. |
| 7,070,686 B2 | 7/2006 | Contolini et al. |
| 7,087,144 B2 | 8/2006 | Herchen |
| 7,285,195 B2 | 10/2007 | Herchen et al. |
| 7,522,055 B2 | 4/2009 | Carrender et al. |
| 7,935,231 B2 | 5/2011 | Ghongadi et al. |
| 7,985,325 B2 | 7/2011 | Rash et al. |
| 8,172,992 B2 | 5/2012 | Prabhakar et al. |
| 8,377,268 B2 | 2/2013 | Rash et al. |
| 8,398,831 B2 | 3/2013 | Ghongadi et al. |
| 8,500,983 B2 * | 8/2013 | Ponnuswamy ........ C23D 3/38 205/103 |
| 9,221,081 B1 | 12/2015 | Mayer et al. |
| 9,228,270 B2 | 1/2016 | Feng et al. |
| 9,476,139 B2 | 10/2016 | Chua et al. |
| 9,746,427 B2 | 8/2017 | Mayer et al. |
| 10,087,545 B2 | 10/2018 | Mayer et al. |
| 10,092,933 B2 | 10/2018 | Kumar et al. |
| 10,196,753 B2 * | 2/2019 | Dinneen ................ C25D 17/16 |
| 2001/0020480 A1 | 9/2001 | Yoshikawa et al. |
| 2002/0000372 A1 | 1/2002 | Pedersen et al. |
| 2002/0020763 A1 | 2/2002 | Hirae et al. |
| 2002/0084183 A1 | 7/2002 | Hanson et al. |
| 2002/0108851 A1 | 8/2002 | Woodruff et al. |
| 2002/0134403 A1 | 9/2002 | Selwyn et al. |
| 2002/0144900 A1 | 10/2002 | Keigler |
| 2002/0153260 A1 | 10/2002 | Egli et al. |
| 2002/0157686 A1 | 10/2002 | Kenny et al. |
| 2003/0010641 A1 | 1/2003 | Kholodenko |
| 2003/0079995 A1 | 5/2003 | Contolini et al. |
| 2003/0085118 A1 | 5/2003 | Tench et al. |
| 2003/0085119 A1 | 5/2003 | Davis et al. |
| 2003/0134044 A1 | 7/2003 | Aoki et al. |
| 2003/0181349 A1 | 9/2003 | Maeno et al. |
| 2003/0201184 A1 | 10/2003 | Dordi et al. |
| 2004/0002430 A1 | 1/2004 | Verhaverbeke |
| 2004/0060576 A1 | 4/2004 | Cronin et al. |
| 2004/0084301 A1 | 5/2004 | Dordi et al. |
| 2004/0112405 A1 | 6/2004 | Lee et al. |
| 2004/0149573 A1 | 8/2004 | Herchen |
| 2004/0171277 A1 | 9/2004 | Oh et al. |
| 2005/0081899 A1 | 4/2005 | Shannon |
| 2005/0183947 A1 | 8/2005 | Henuset |
| 2005/0218000 A1 | 10/2005 | Hafezi et al. |
| 2005/0284754 A1 | 12/2005 | Herchen et al. |
| 2005/0287928 A1 | 12/2005 | Hardikar et al. |
| 2006/0113192 A1 | 6/2006 | Kurashina et al. |
| 2006/0118132 A1 | 6/2006 | Bergman et al. |
| 2006/0151007 A1 | 7/2006 | Bergman |
| 2006/0226000 A1 | 10/2006 | Hanson et al. |
| 2006/0237308 A1 | 10/2006 | Herchen |
| 2006/0246690 A1 | 11/2006 | Dordi et al. |
| 2006/0266653 A1 | 11/2006 | Birang et al. |
| 2007/0077871 A1 | 4/2007 | Park et al. |
| 2007/0141849 A1 | 6/2007 | Kanno et al. |
| 2007/0199578 A1 | 8/2007 | Nomura et al. |
| 2008/0011322 A1 | 1/2008 | Weber et al. |
| 2008/0117051 A1 | 5/2008 | Carrender et al. |

(56) References Cited

U.S. PATENT DOCUMENTS

| | | |
|---|---|---|
| 2009/0009753 A1 | 1/2009 | Horai et al. |
| 2009/0033889 A1 | 2/2009 | Bleeker et al. |
| 2009/0107835 A1 | 4/2009 | Ghongadi et al. |
| 2009/0107836 A1 | 4/2009 | Rash et al. |
| 2009/0117730 A1 | 5/2009 | Maitani et al. |
| 2010/0116290 A1 | 5/2010 | Zhu et al. |
| 2010/0144158 A1 | 6/2010 | Ito et al. |
| 2010/0155254 A1 | 6/2010 | Prabhakar et al. |
| 2010/0216302 A1 | 8/2010 | Luo et al. |
| 2011/0181000 A1 | 7/2011 | Ghongadi et al. |
| 2011/0217848 A1 | 9/2011 | Bergman et al. |
| 2011/0233056 A1 | 9/2011 | Rash et al. |
| 2012/0043200 A1 | 2/2012 | Fujikata et al. |
| 2012/0137970 A1 | 6/2012 | Naruse et al. |
| 2012/0174827 A1 | 7/2012 | Sekiguchi et al. |
| 2012/0181170 A1 | 7/2012 | Prabhakar et al. |
| 2012/0261254 A1* | 10/2012 | Reid ................ C25D 7/123 204/227 |
| 2013/0042454 A1 | 2/2013 | Feng et al. |
| 2013/0062197 A1 | 3/2013 | He et al. |
| 2013/0256146 A1 | 10/2013 | Chua et al. |
| 2013/0292254 A1 | 11/2013 | Kumar et al. |
| 2014/0230855 A1 | 8/2014 | Mayer et al. |
| 2014/0367265 A1 | 12/2014 | Ravid et al. |
| 2015/0218726 A1 | 8/2015 | Feng et al. |
| 2016/0145761 A1 | 5/2016 | Mayer et al. |
| 2016/0186355 A1 | 6/2016 | Feng et al. |
| 2016/0201212 A1 | 7/2016 | Ostrowski et al. |
| 2017/0009369 A1 | 1/2017 | Berke et al. |
| 2017/0009370 A1 | 1/2017 | Chua et al. |
| 2017/0073832 A1 | 3/2017 | Berke et al. |
| 2017/0299524 A1 | 10/2017 | Arora et al. |

FOREIGN PATENT DOCUMENTS

| | | |
|---|---|---|
| CN | 1623012 A | 6/2005 |
| CN | 1930666 A | 3/2007 |
| CN | 100469948 C | 3/2009 |
| CN | 101599420 | 12/2009 |
| CN | 101798698 | 8/2010 |
| CN | 102953104 A | 3/2013 |
| CN | 103031580 A | 4/2013 |
| EP | 1 724 820 A1 | 11/2006 |
| JP | 2002-069698 | 3/2002 |
| JP | 2002-540011 | 11/2002 |
| JP | 2004-052059 A | 2/2004 |
| JP | 2004-83932 | 3/2004 |
| JP | 2004-247738 | 9/2004 |
| JP | 2004-270014 | 9/2004 |
| JP | 2005-146398 | 6/2005 |
| JP | 2007-204832 | 8/2007 |
| JP | 2007-521391 A | 8/2007 |
| JP | 2008-045179 | 2/2008 |
| JP | 2008-95157 | 4/2008 |
| JP | 2010-150659 | 7/2010 |
| JP | 2014-019900 A | 2/2014 |
| JP | 2014-196555 A | 10/2014 |
| JP | 2015-071802 A | 4/2015 |
| JP | 2018-119176 A | 8/2018 |
| JP | 2019-002065 A | 1/2019 |
| KR | 10-2004-0079843 | 9/2004 |
| KR | 10-2004-0081577 | 9/2004 |
| KR | 10-2005-0068038 | 7/2005 |
| KR | 10-2007-0064847 | 6/2007 |
| KR | 10-2008-0007931 | 1/2008 |
| TW | 531770 | 5/2003 |
| TW | 544811 | 8/2003 |
| TW | 200409836 | 6/2004 |
| TW | 200410296 A | 6/2004 |
| TW | 200511422 A | 3/2005 |
| TW | I244548 | 12/2005 |
| TW | 2009/16796 A | 4/2009 |
| TW | 2009/16976 A | 4/2009 |
| TW | I585246 B | 6/2017 |
| WO | WO 99/041434 | 8/1999 |
| WO | WO 03/006718 | 1/2003 |
| WO | WO 03/010368 A | 2/2003 |
| WO | WO 2013/148890 | 10/2013 |

OTHER PUBLICATIONS

Taiwanese First Office Action dated May 7, 2018 issued in Application No. TW 103104954.

Ham, et al. (2007) "Electroplating Apparatus for Semiconductor Wafer," Patent Abstract & Machine Translation, KR 10-2007-0064847A, pp. 1-7.

U.S. Notice of Allowance [Corrected Notice of Allowability], dated Jul. 21, 2017, issued in U.S. Appl. No. 14/178,804.

U.S. Notice of Allowance, dated Aug. 7, 2017, issued in U.S. Appl. No. 14/685,526.

U.S. Notice of Allowance, dated Feb. 6, 2018, issued in U.S. Appl. No. 14/685,526.

U.S. Office Action, dated Sep. 21, 2017, issued in U.S. Appl. No. 14/990,725.

U.S. Notice of Allowance, dated Sep. 1, 2017, issued in U.S. Appl. No. 14/936,328.

U.S. Notice of Allowance, dated Apr. 12, 2018, issued in U.S. Appl. No. 14/936,328.

U.S. Office Action, dated Oct. 31, 2017, issued in U.S. Appl. No. 15/004,593.

U.S. Notice of Allowance, dated Feb. 7, 2018, issued in U.S. Appl. No. 14/949,681.

U.S. Office Action, dated Sep. 7, 2017, issued in U.S. Appl. No. 14/957,156.

U.S. Final Office Action, dated Mar. 21, 2018, issued in U.S. Appl. No. 14/957,156.

U.S. Final Office Action, dated Aug. 25, 2017, issued in U.S. Appl. No. 13/852,767.

Japanese Decision to Grant w/Search Report dated Mar. 27, 2018 issued in Application No. JP 2014-026848.

Chinese First Office Action dated Jun. 20, 2017 issued in Application No. CN 201510837221.9.

Chinese Second Office Action dated Feb. 24, 2018 issued in Application No. CN 201510837221.9.

Taiwan Office Action, dated Jul. 11, 2017, issued in Application No. TW 106105154.

Taiwan Notice of Allowance and Search Report, dated Sep. 8, 2017, issued in Application No. TW 102111465.

Chinese First Office Action dated Jan. 29, 2018, issued in CN 201610539196.0.

DuPont Teflon, *Dupont*, May 2015, 5pp [Downloaded on Oct. 11, 2017 at https://web.archive.org/web/20150301000000*https://plastics.ulprospector.com/generics/41/c/t/polyphenlene-sulfide-pps-properties-processing].

Guide to Whitford Industrial Coatings 2012, *Whitford Worldwide*, 3pp [Downloaded on Oct. 11, 2017 at https://web.archive.org/web/*/http://efpadm2.itum.com/files/files/rpn/7.pdf] (Year: 2012).

*Merriam-Webster Dictionary*, Definition of "Integrate" [Downloaded on Aug. 28, 2017 at https://www.merriam-webster.com/dictionary/integrate], 12pp.

*Wikipedia, the free encyclopedia*, Definition of "Through hole" [Downloaded on Aug. 24, 2017 from https://en.wikipedia.org/wiki/Through_hole, 1 page.

International Search Report and Written Opinion dated Oct. 26, 2018 issued in Application No. PCT/US2018/039827.

Chinese First Office Action dated Jun. 20, 2017 issued in CN 201510837221.9.

U.S. Office Action, dated Nov. 23, 2016, issued in U.S. Appl. No. 14/178,804.

U.S. Notice of Allowance, dated May 3, 2017, issued in U.S. Appl. No. 14/178,804.

U.S. Office Action, dated Mar. 6, 2017, issued in U.S. Appl. No. 14/685,526.

U.S. Office Action, dated Nov. 1, 2011, issued in U.S. Appl. No. 12/633,219.

(56) References Cited

OTHER PUBLICATIONS

U.S. Notice of Allowance, dated Jan. 12, 2012, issued in U.S. Appl. No. 12/633,219.
U.S. Notice of Allowance, dated Mar. 19, 2012, issued in U.S. Appl. No. 12/633,219.
U.S. Office Action, dated Oct. 26, 2012, issued in U.S. Appl. No. 13/432,767.
U.S. Final Office Action, dated Nov. 26, 2013, issued in U.S. Appl. No. 13/432,767.
U.S. Office Action, dated Nov. 6, 2014, issued in U.S. Appl. No. 13/563,619.
U.S. Final Office Action, dated Apr. 23, 2015, issued in U.S. Appl. No. 13/563,619.
U.S. Notice of Allowance, dated Aug. 31, 2015, issued in U.S. Appl. No. 13/563,619.
U.S. Notice of Allowance [corrected Notice of Allowability], dated Sep. 23, 2015, issued in U.S. Appl. No. 13/563,619.
U.S. Office Action, dated Feb. 23, 2015, issued in U.S. Appl. No. 13/584,343.
U.S. Notice of Allowance, dated Aug. 31, 2015, issued in U.S. Appl. No. 13/584,343.
U.S. Office Action, dated Mar. 2, 2011, issued in U.S. Appl. No. 11/929,638.
U.S. Notice of Allowance, dated May 23, 2011, issued in U.S. Appl. No. 11/929,638.
U.S. Office Action, dated Jul. 7, 2010, issued in U.S. Appl. No. 11/932,595.
U.S. Office Action, dated Nov. 17, 2010, issued in U.S. Appl. No. 11/932,595.
U.S. Notice of Allowance, dated Jan. 26, 2011, issued in U.S. Appl. No. 11/932,595.
U.S. Notice of Allowance, dated Mar. 8, 2011, issued in U.S. Appl. No. 11/932,595.
U.S. Notice of Allowance (Supplemental Notice of Allowability) dated Mar. 11, 2011, issued in U.S. Appl. No. 11/932,595.
U.S. Notice of Allowance, dated Mar. 18, 2011, issued in U.S. Appl. No. 11/932,595.
U.S. Office Action, dated Nov. 4, 2011, issued in U.S. Appl. No. 13/154,224.
U.S. Office Action, dated Mar. 16, 2012, issued in U.S. Appl. No. 13/154,224.
U.S. Final Office Action, dated Jul. 18, 2012, issued in U.S. Appl. No. 13/154,224.
U.S. Notice of Allowance, dated Oct. 4, 2012, issued in U.S. Appl. No. 13/154,224.
U.S. Notice of Allowance (Corrected Notice of Allowability) dated Jan. 23, 2013, issued in U.S. Appl. No. 13/154,224.
U.S. Office Action, dated May 21, 2012, issued in U.S. Appl. No. 13/079,745.
U.S. Office Action, dated Sep. 21, 2012, issued in U.S. Appl. No. 13/079,745.
U.S. Notice of Allowance, dated Nov. 19, 2012, issued in U.S. Appl. No. 13/079,745.
U.S. Notice of Allowance, dated Jun. 30, 2016, issued in U.S. Appl. No. 13/853,935.
U.S. Office Action, dated Oct. 28, 2015, issued in U.S. Appl. No. 13/852,767.
U.S. Final Office Action, dated Apr. 28, 2016, issued in U.S. Appl. No. 13/852,767.
U.S. Office Action, dated Feb. 24, 2017, issued in U.S. Appl. No. 13/852,767.
Chinese First Office Action dated May 2, 2013 issued in CN 200910211989.X.
Japanese Office Action, dated Oct. 2, 2012, issued in Application No. JP 2009-278998.
Korean Description of Notification of Provisional Rejection, dated May 10, 2012, issued in Application No. KR 2009-0122738.
Korean Notification of Decision to Grant, dated Sep. 4, 2012, issued in Application No. KR 2009-0122738.
Singapore Search Report and Written Opinion, dated Mar. 9, 2011, issued in Application No. SG 200908245.4.
Singapore Search and Examination Report, dated Oct. 27, 2011, issued in Application No. SG 200908245.4.
Taiwan International Search Report, dated Jun. 11, 2012, issued in Application No. TW 098142112.
Chinese First Office Action dated Jan. 26, 2016, issued in Application No. CN 201210289735.1.
Chinese Second Office Action dated Nov. 2, 2016, issued in Application No. CN 201210289735.1.
Japanese First Office Action dated Jun. 28, 2016, issued in Application No. JP 2012-179853.
Japanese Second Office Action dated Mar. 14, 2017, issued in Application No. JP 2012-179853.
Singapore Search Report and Written Opinion, dated Oct. 6, 2014, issued in Application No. SG 201206129-7.
Singapore Final Exam Report, dated May 20, 2015, issued in Application No. SG 201206129-7.
Taiwan Office Action and Search Report, dated May 12, 2016, issued in Application No. TW 101129602.
PCT International Search Report and Written Opinion dated Jul. 25, 2013 issued in PCT/US2013/034178.
PCT International Preliminary Report on Patentability and Written Opinion dated Oct. 9, 2014 issued in PCT/US2013/034178.
Chinese First Office Action dated Mar. 2, 2016 issued in Application No. CN 201380023757.6.
Chinese Second Office Action dated Jan. 24, 2017 issued in Application No. CN 201380023757.6.
Taiwan Examination and Search Report dated Oct. 12, 2016, issued in TW 102111233.
*Cambridge English Dictionary*, Meaning of "against" (2016), 2 pages.
Everett, D.H. (2001) "Definition of Surface Active Agents," *Manual of Symbols and Terminology for Physicochemical Quantities and Units*, Appendix II, *International Union of Pure and Applied Chemistry, Division of Physical Chemistry*, Adopted by the IUPAC Council at Washington DC, USA on Jul. 23, 1971, 6pp.
Shin-Etsu Polymer Co., Ltd., "L-type connector," http://www.shinpoly.co.jp./business/connector/products_e/l/html?typezeb (one page) downloaded May 23, 2003.
Shin-Etsu Polymer Co., Ltd., "SS-type connector," http://www.shinpoly.co.jp./business/connector/products_e/ss.html?typezeb (2 pages) downloaded May 23, 2003.
Zheng, CN 101599420a, abstract and machine translation (2009).
U.S. Office Action, dated Feb. 4, 2019, issued in U.S. Appl. No. 15/276,436.
Japanese First Office Action dated May 30, 2019 issued in Application No. LAMRP033JPD1.
Taiwanese First Office Action dated Jul. 3, 2019 issued in Application No. TW 108104390.

\* cited by examiner

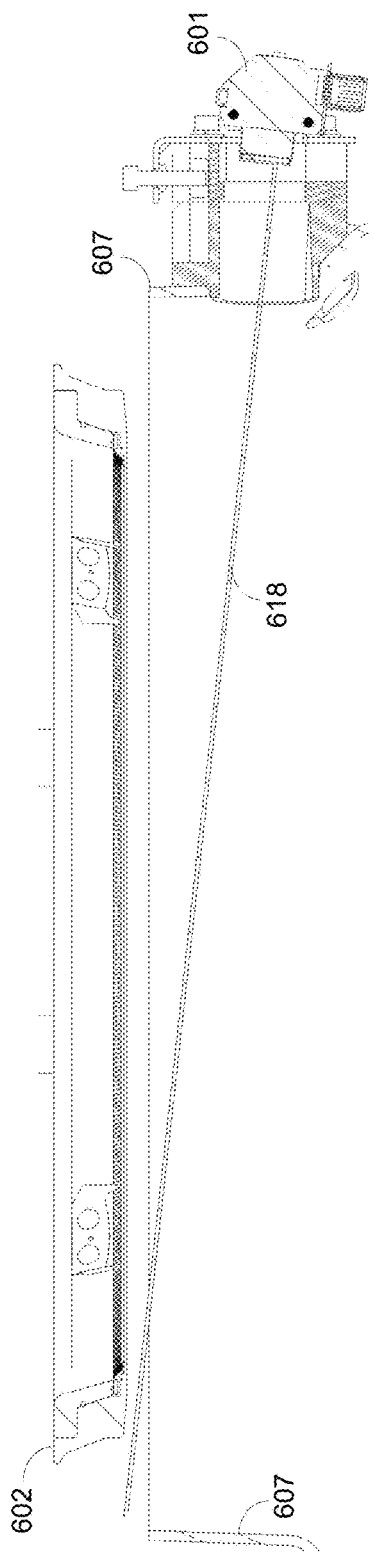
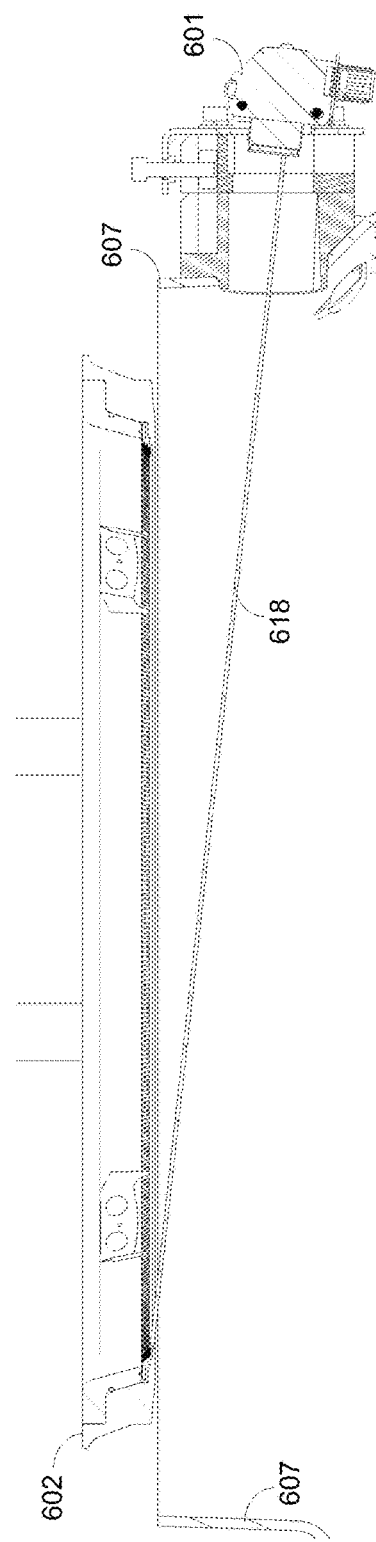
FIG. 6A
FIG. 6B

| Run # | % plating |
|---|---|
| 1 | 19.87 |
| 2 | 19.99 |
| 3 | 19.97 |
| 4 | 20.25 |
| 5 | 19.96 |
| 6 | 19.96 |
| 7 | 20.39 |
| 8 | 20.14 |
| 9 | 20.15 |
| 10 | 20.15 |
| Stdev | 0.15 |

REMOTE DETECTION OF PLATING ON WAFER HOLDING APPARATUS

CROSS REFERENCE TO RELATED APPLICATIONS

This application is a continuation-in-part of U.S. patent application Ser. No. 14/178,804, filed Feb. 12, 2014, and titled "DETECTION OF PLATING ON WAFER HOLDING APPARATUS," which claims benefit of priority to U.S. Provisional Patent Application No. 61/765,502, filed Feb. 15, 2013, each of which is herein incorporated by reference in its entirety and for all purposes.

BACKGROUND

Recent advances in semiconductor fabrication and processing have led to increased use of electroplating to deposit a variety of materials on semiconductor devices. Such materials include electroplated copper, nickel, and tin-silver alloys.

SUMMARY

Certain embodiments herein relate to methods, apparatus, and a drip shield for detecting the presence or absence of an unwanted metal deposit on a substrate holder of an electroplating apparatus.

In one aspect of the embodiments herein, an electroplating apparatus is provided, the apparatus including: an electrolyte vessel configured to hold electrolyte during electroplating; a substrate holder configured to support a substrate during electroplating, where the substrate holder is annularly shaped and supports the substrate at its periphery, the substrate holder including a sensor target area; and a plating sensor including a light source aimed at the sensor target area, where the plating sensor distinguishes between (i) areas on the sensor target area where unwanted metal deposits are present and (ii) areas on the sensor target area where unwanted metal deposits are absent.

In various embodiments, the substrate holder includes a cup and a lip seal, the cup including a bottom surface and an inner wall, where the lip seal is positioned at the top of the inner wall of the cup. In some such cases, the sensor target area is on the lip seal. In other cases, the sensor target area is on the inner wall of the cup. In certain cases, the sensor target area is on both the inner wall of the cup and the lip seal.

The electroplating apparatus may further include a drip shield. The plating sensor may be positioned on the drip shield. The drip shield may include a wall and a central opening through which the substrate holder fits. The wall may be a peripheral wall that defines the central opening. In a particular embodiment, the apparatus includes a drip shield, where the plating sensor is positioned on the drip shield. In these or other cases, the drip shield may include a wall and a central opening through which the substrate holder fits. The plating sensor may be various types of sensors. For instance, the plating sensor may be a color-based sensor, an intensity-based sensor, or a camera.

In one embodiment, the electroplating apparatus further includes an alignment fixture that fits over the substrate holder, the alignment fixture including a first portion and a second portion, where the first and second portions are distinguishable from one another with respect to a property measured by the plating sensor. In some such embodiments, the substrate holder includes a cup and a lip seal, the cup including a bottom surface and an inner wall, where the lip seal is positioned at the top of the inner wall of the cup, and where the first portion of the alignment fixture is proximate the lip seal such that the plating sensor detects the presence or absence of metal deposits on the lip seal. In another embodiment, the substrate holder includes a cup and a lip seal, the cup including a bottom surface and an inner wall, where the lip seal is positioned at the top of the inner wall of the cup, and where the first portion of the alignment fixture is proximate the inner wall of the cup such that the plating sensor detects the presence or absence of metal deposits on the inner wall of the cup.

The electroplating apparatus may further include a dryer that dries the sensor target area. In some such cases, the electroplating apparatus may further include a controller having executable instructions to dry the sensor target area prior to detecting the presence or absence of unwanted metal deposits using the plating sensor. In these or other cases, the substrate holder may be rotatable with respect to the plating sensor. In a number of embodiments, the electroplating apparatus includes an inlet configured to deliver fluid to the sensor target area. In some such cases, the electroplating apparatus may further include a controller having executable instructions to wet the sensor target area with fluid after the plating sensor is used to detect the presence or absence of unwanted metal deposits in the sensor target area and before the electroplating apparatus is used to electroplate on a new substrate.

In another aspect of the embodiments herein, a drip shield for an electroplating apparatus is provided, the drip shield including: a peripheral wall having a substantially similar diameter as an electrolyte vessel in the electroplating apparatus; a central opening through which a substrate holder of the electroplating apparatus can fit, the central opening being defined by the peripheral wall; and a plating sensor mounted on the peripheral wall.

In some embodiments, the drip shield includes a shutter proximate the plating sensor, where the shutter can be closed to physically separate the plating sensor from the electrolyte vessel of the electroplating apparatus. In some cases, the drip shield includes a window proximate the plating sensor, where the plating sensor can sense through the window of the drip shield. In some implementations, the drip shield includes a peripheral opening in the peripheral wall proximate the plating sensor, where the plating sensor can sense through the peripheral opening.

In another aspect of the disclosed embodiments, a method of detecting the presence or absence of an unwanted metal deposit on a substrate holder of an electroplating apparatus is provided, the method including: positioning the substrate holder at a detection position, the substrate holder including a sensor target area; and operating a plating sensor including a light source to detect the presence or absence of the unwanted metal deposit in the sensor target area, where the plating sensor and the sensor target area are positioned on opposite sides of the electroplating apparatus such that a line of sight of the plating sensor extends across the electroplating apparatus.

These and other features will be described below with reference to the associated drawings.

BRIEF DESCRIPTION OF THE DRAWINGS

FIGS. 6A and 6B show a portion of an electroplating apparatus, particularly a drip shield with a plating sensor installed thereon.

DETAILED DESCRIPTION

Figure 1:
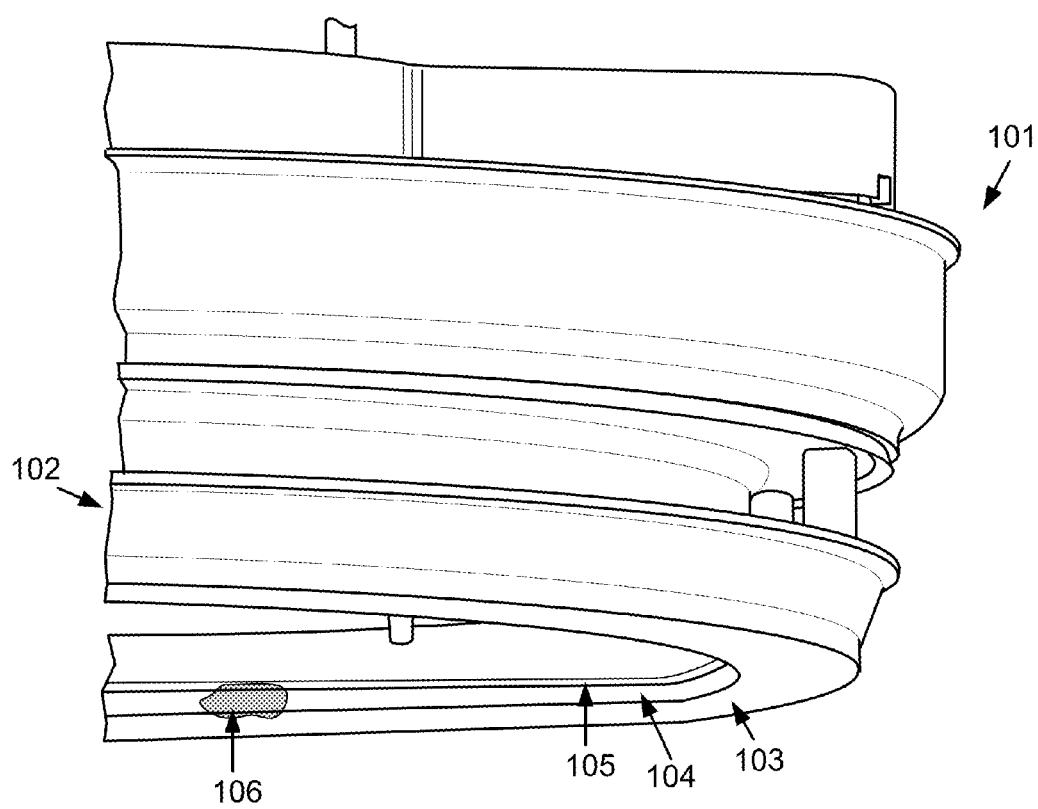
FIG. 1 illustrates a substrate holder of an electroplating apparatus having an unwanted metal deposit thereon.

In this application, the terms "semiconductor wafer," "wafer," "substrate," "wafer substrate," and "partially fabricated integrated circuit" are used interchangeably. One of ordinary skill in the art would understand that the term "partially fabricated integrated circuit" can refer to a silicon wafer during any of many stages of integrated circuit fabrication thereon. A wafer or substrate used in the semiconductor device industry typically has a diameter of 200 mm, or 300 mm, or 450 mm. Further, the terms "electrolyte," "plating bath," "bath," and "plating solution" are used interchangeably. The following detailed description assumes the embodiments are implemented on a wafer. However, the embodiments are not so limited. The work piece may be of various shapes, sizes, and materials. In addition to semiconductor wafers, other work pieces that may take advantage of the disclosed embodiments include various articles such as printed circuit boards, magnetic recording media, magnetic recording sensors, mirrors, optical elements, micro-mechanical devices and the like.

In the following description, numerous specific details are set forth in order to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

While the discussion herein focuses on substrate holders constructed with a cup and lip seal, other arrangements may be used. Generally, when the terms "cup bottom" or "substrate holder bottom" are used herein, these terms are intended cover the bottom of any wafer holder, regardless of whether that wafer holder is constructed with a cup as depicted in the figures. The bottom surface of a wafer holder is generally the side of the wafer holder facing into the electroplating solution. It is typically oriented in substantially the same direction as the face of a substrate being plated, and is often nominally planar to the wafer. The cup of the wafer holder may also include an inner wall (sometimes referred to as an inner surface), which may extend upwards from the bottom surface of the substrate holder, either vertically or at an angle. The inner wall may have an annular shape, having a diameter slightly smaller than the diameter of the substrate. Typically, the substrate holder is positioned around the peripheral portion of a substrate (such that the substrate holder supports the edges of the substrate), and extends radially outward from the substrate. As used herein, the term lip seal generally refers to a portion of the wafer holder that engages with the edge of the wafer and creates a seal that protects the interior of the wafer holder (including the electrical contacts for connecting to the wafer) from electroplating solution while exposing the entire plating face of the wafer to electroplating solution. The lip seal may be situated at the top of the inner wall of the cup of the substrate holder. Any of a variety of lip seal designs may be used.

For simplicity and clarity, most of the examples herein concern wafer-face-down, "fountain" plating apparatus. In such apparatus, the work piece to be plated (typically a semiconductor wafer or other substrate) generally has a substantially horizontal orientation (which may in some cases vary by a few degrees from true horizontal for some part of, or during the entire plating process) and may be powered to rotate during plating, yielding a generally vertically upward electrolyte convection pattern. Integration of the impinging flow mass from the center to the edge of the wafer, as well as the inherent higher angular velocity of a rotating wafer at its edge relative to its center creates a radially increasing sheering (wafer parallel) flow pattern. Clamshell-type electroplating apparatus having a cup and cone arrangement are frequently used to hold wafers in place before and during electroplating. Examples of clamshell and fountain plating cells/apparatus are included in the Sabre® family of Electroplating Systems produced by and available from Lam Research, Inc. of Fremont, Calif. Additionally, clamshell fountain electroplating systems are described in, e.g., U.S. Pat. No. 6,800,187 filed Aug. 10, 2001 and U.S. Pat. No. 8,308,931 filed Feb. 11, 2010, which are incorporated herein by reference in their entireties. While the description herein focuses primarily on an orientation with the wafer and the holder face down, parallel to the plane of the local earth's surface, it is understood that other orientations, such as angled or normal to the earth surface are not excluded and also envisioned.

Furthermore, while the discussion and examples herein generally focus on the detection of tin/silver buildup, the embodiments may be practiced to detect the presence of any material in the region where the detector is focused.

Unwanted Metal Deposits on Substrate Holder

Problems associated with spurious metal deposits on lip seals and cup bottoms are exacerbated as wafers are designed with more and more features near the edge of the wafers, where they are especially likely to be impacted by such plating. Further, the presence of near edge features promotes generation of spurious deposits on wafer holders and seals. The interference between near-edge features and the lip seal plating is much greater when the density of features near the edge is high. The drive towards more near-edge features results from a desire to maximize the number of semiconductor devices that can be obtained from a single wafer.

In the examples presented herein, an electroplating apparatus includes a cup to support a wafer during plating. The cup holds the wafer in place by supporting the outer periphery of the wafer. The cup therefore has a large opening in its center, the opening having a slightly smaller diameter than the diameter of the wafer. FIG. 1 shows a wafer positioning system 101 including a cup 102. In certain cases, the cup 102 may be coated with a material having non-sticking characteristics, such as polyvinlyidene fluoride (PVDF, e.g., Kynar® from Arkema of Colombes, France) or polytetrafluorethleyene (PTFE, e.g., Teflon® from Dupont of Wilmington, Del.), silicones, or silicon and oxygen glass-like ceramic non-stick materials such as Cuisinart's "Ceramica™" or Thermolon™.

In one example, the cup 102 includes a bottom surface 103 and an inner wall 104 (also referred to as an inner surface 104). The inner wall 104 may be vertically oriented, substantially perpendicular to the bottom surface 103 of the cup 102. The inner wall 104 may also be oriented at a non-vertical angle. The inner wall 104 may have a height between about 1.0-1.5 mm in certain cases. A lip seal 105 is positioned at the top of the inner wall 104, and engages with the wafer during plating, which forms a peripheral seal. The lip seal 105 may have a height between about 0.75-1.5 mm in certain embodiments. During electroplating, the lip seal 105 protects electrical contacts (not shown) which are located radially outside of the lip seal 105. At the bottom of the cup's inner wall 104, the cup 102 extends horizontally radially outward (radially outwards and parallel to the wafer). This horizontal surface is the bottom surface 103 of the cup 102.

While undesired plating on the cup itself initially begins on the cup's inner wall 104 where the cup 102 meets the lip seal 105, the plating can progress down this inner wall 104, around the corner of the cup 102, and radially outward on the bottom surface 103 of the cup 102. An undesired metal deposit is shown as element 106. When the undesired metal deposit 106 reaches the bottom surface 103, significant manufacturing defects can occur, and wafers that are processed while there is plating on the bottom surface 103 of the cup 102 are often ruined or have very low yields. The transition to cup bottom plating and growth is due in part to the fact that the metal more easily adheres onto the cup 102 (especially the bottom surface 103) as compared to the lip seal 104. Although the bottom surface 103 and other parts of the cup 102 may be coated with non-stick coatings such as a fluorinated polymer coating (e.g., polytetrafluoroethylene, PTFE) to help discourage metal from attaching to this surface, deposits can still form on the bottom surface 103 from time to time. In many cases, once plating starts to occur on the bottom surface 103, the rate of deposition substantially increases and the deposition can quickly become out of control and plate the entire bottom surface 103.

Because tin-silver alloys are often deposited toward the end of semiconductor manufacturing processes (for example, as tin-silver solder contacts), the wafers used in the tin-silver deposition process are typically very expensive, having been through many processing operations before they reach this point in the overall production process. Therefore, the failure to detect plating on the substrate holder (which may lead to fabrication of wafers that are low yield or out of specification) can be especially costly.

Without being limited to a particular theory, it is believed that spurious deposition of tin-silver alloy occurs as a result, at least in part, of the significantly differing reduction potentials of atomic tin versus atomic silver. Furthermore, it is believed that growth of spurious deposits occurs first by the plating of tin (with little silver content) at the lip seal wafer interface, then through a displacement reaction (Sn+ 2Ag$^+$→Sn$^{2+}$+2Ag) on the surface of the lip seal and cup, resulting in a substitution of two silver atoms (having oxidation state+1) for every atom of tin (having oxidation state+2) and a corresponding growth in the volume of the spurious film. Once again, without being limited to a particular theory, it is believed that other metal or alloy deposits formed from metals having significantly different reduction potential, for example, having a reduction potential difference greater than about 100 mV or more, may lead to the same or similar problems involving spurious metallic deposition on the lip seal and cup of an electroplating assembly.

Metal deposits on the bottom and inner surfaces of the cup can lead to both (1) local non-uniformities in the region near the unwanted deposit due to local variations in current and potential distribution, as well as (2) a decrease in the average thickness of the film deposited over the entire wafer. The loss of yield therefore is not only related to the generation of stray metallic particles, but also due to the scavenging or "current sinking" of charge intended for plating on the wafer itself. The first impact is generally local to the region on the wafer around where the unwanted plating has occurred, as locally, current is drawn away from the features near the edge of the substrate to the bottom and inner surfaces of the cup, making near edge features thinner than desired. With increasing extent of unwanted plating on the cup, the second impact (thinner than desired average plating thickness over the entire wafer) occurs as the total amount of current plated on the cup itself becomes significant relative to the total amount of current needed to plate the entire wafer, and therefore, the average thickness of the features plated on the wafer drops below a target average thickness.

Substrates that have lower amounts of open area (areas where electroplating is desired) are more sensitive to the presence of unwanted plating on substrate holders compared to substrates that have higher amounts of open area. These low open area/low feature density substrates are more sensitive due to the fact that the ratio of unwanted plating area on the cup to desired substrate plating area is relatively high. In other words, because the area in which current should be delivered to the substrate is small, it is easy to redirect a substantial amount of this current when unwanted plating is present on the cup. By contrast, for high open area/high feature density substrates, the area where current is desired to be delivered is larger. As such, the initiation of unwanted plating on the cup will draw off a relatively smaller portion of the current delivered to the wafer. In both cases, it is beneficial to immediately detect small amounts of plating as quickly as possible to avoid processing wafers that do not plate with the target uniformity or average thickness.

In both plating problems listed above, the harmful effects occur because the metal deposit effectively scavenges current from the surface of the wafer (where it is desired) and redirects it to the metal deposit itself (where it undesirably causes even more plating to occur at the site of the deposit). In many tin/silver deposition processes such as the formation of the relatively low I/O count bumps on memory devices, the amount of open area on the wafer (e.g., the area where current is intended to be directed and where plating occurs) can be very small (e.g., about 0.5-3% of the face of the wafer). Therefore, the current is directed to a fairly small area on wafer, which may be comparable to size of a metallic deposit on the cup. In part because these two areas are comparable in size, a proportionately large amount of the current that should be directed to the open areas on the wafer is instead directed to the deposit on the cup. Thus, the formation of even a small amount of plating on the bottom or inner surface of the cup can significantly impact the wafer's plating around that feature. Moreover, if the deposit is sufficiently large, it can impact the overall plated thickness on the wafer. Of course, this can cause failure of many or all dies on a wafer. The area of the bottom surface of a cup for supporting a 300 mm wafer is typically approximately 200 $cm^2$. The exposed area of a 300 mm wafer is about 700 $cm^2$. If a 300 mm wafer is masked to expose a small portion, e.g., 1%, of the wafer surface, the plating area on the wafer is about 7 $cm^2$. If a very small portion of the cup bottom, for example if only about 0.5% of the cup bottom, or about a 1×1 cm segment (1 $cm^2$) ends up plated, the average rate of plating on wafer could decrease by a substantial amount, for example by about 14% (100*1 $cm^2$/7 $cm^2$=14%).

Cleaning Processes to Remove Unwanted Metal Deposits

Because spurious tin/silver buildup can lead to the outlined problems, it is important that tin/silver deposits be detected and then removed or cleaned away from the lip seal and cup bottom, or the cup bottom and lip seal be replaced. Different cleaning techniques may be used to remove the unwanted deposits. In some cases, the cleaning may be done on an automated basis. In other cases, cleaning may be initiated and/or performed manually. Example techniques for cleaning a substrate holder are further discussed and described in the following U.S. Patents and Patent Applications, each of which is incorporated by reference herein in its entirety: U.S. Pat. No. 9,221,081, titled "AUTOMATED CLEANING OF WAFER PLATING ASSEMBLY"; U.S. Pat. No. 9,476,139, titled "CLEANING ELECTROPLATING SUBSTRATE HOLDERS USING REVERSE CURRENT DEPLATING"; and U.S. patent application Ser. No. 13/852,767, filed Mar. 28, 2013, and titled "METHODS AND APPARATUSES FOR CLEANING ELECTROPLATING SUBSTRATE HOLDERS."

Once plating occurs on the bottom surface of the cup, the deposit often cannot be removed by an autoclean process, and must instead be removed through a different process such as dipping or manual swiping to chemically etch the cup (e.g., using a chemical solution mixture of concentrated nitric acid with or without hydrogen chloride to manually remove the deposits). As such, it is highly beneficial to remove such deposits before they grow to reach the bottom surface of the cup.

In some embodiments, the cleaning technique involves shooting a jet of cleaning fluid (e.g., deionized water or other cleaning fluid) in the direction of the lip seal/bottom surface/inner wall of the cup. The cleaning fluid removes the tin/silver buildup as the substrate holder and cleaning fluid jet rotate with respect to one another.

Various different cleaning agents/fluids may be used. In some embodiments, selection of the cleaning agent will depend on the composition of the unwanted deposits to be removed. For instance, removal of unwanted tin-silver alloy deposits may successfully employ an oxidizing acid solution into which both tin and silver metal and salts are oxidizable and/or soluble. Thus, in some embodiments, the cleaning agent may include an acid and/or oxidizing agent. A particular example of an appropriate cleaning agent or cleaning solution for removing tin-silver alloy deposits is a solution of nitric acid. Such a solution may have, for example, a nitric acid concentration of about or greater than 5%, 10%, 15%, 20%, 25%, 35%, or 50% by weight; or about or less than any one of these concentrations; or within a range defined by any pair of these concentrations. In some embodiments, a cleaning agent/solution may employ multiple acids, such as, for instance, a combination of nitric acid and hydrochloric acid (i.e., to form aqua regia) with both acids present in any of the above recited concentrations or within the above recited ranges of concentrations. However, other acids and combinations of acids may also be employed—again, in any of the above recited concentrations or recited ranges of concentrations. In some embodiments, the cleaning agent may be a metal complexing agent, and typically a complexing agent selected for its ability to complex a metal making up the deposits to be removed. For instance, a complexing agent selected as a cleaning agent may be oxalate ion since it complexes tin. In some embodiments, a silver complexing agent may be selected as a cleaning agent, such as various mercapto-derivative compounds.

One alternative cleaning method includes rotating a cleaning disc that has cleaning fluid therein, where the rotation results in the cleaning fluid emanating from peripheral pores in the disc. The cleaning solution then contacts the substrate holder to remove the unwanted deposits. In some embodiments, the disc may have a substantially circular upper surface, a substantially circular lower surface, a substantially circular edge joining the upper and lower surfaces, and a plurality of pores opening at the edge. The disc may also have an interior region extending into the interior of the disc. In some embodiments, the pores are dimensioned such that the cleaning agent is retained in the interior of the pores by an adhesive force between the cleaning agent and the interior surface of the pores. One method of using such a cleaning disc may involve loading a cleaning agent into a plurality of pores of the cleaning disc, positioning the cleaning disc within a semiconductor processing apparatus, and rotating the disc or otherwise manipulating the disc to release cleaning agent from the plurality of pores such that elements of the apparatus are contacted by the released cleaning agent. This cleaning technique and apparatus therefore are further described in U.S. Pat. No. 9,221,081, which was incorporated by reference above.

Another alternative autocleaning technique involves reverse current deplating. Such cleaning involves positioning a cleaning (deplating) disc in an electroplating cup similar to a regular processed substrate. The front surface of the cleaning disc includes a corrosion resistant conductive material to form electrical connections to deposits on the cup's surfaces. The disc is sealed in the cup and submerged into a plating solution. A reverse current (i.e., a current that is opposite that typically used to plate material on a substrate) is then applied to the front conductive surface of the disc to initiate deplating of the deposits. Sealing compression in the cup may change during cleaning to cause different deformation of the lip seal and to form new electrical connections to the deposits. This cleaning technique is further described in U.S. Pat. No. 9,476,139, which was incorporated by reference above.

Before autocleaning was implemented, cleaning generally took place manually. An operator would use a swab dipped in concentrated nitric acid solution or other reagent capable of dissolving metal to remove the metal buildup. The operator was able to visually inspect the lip seal and cup bottom to ensure complete removal of the metal. Of course, this was a time consuming and inefficient process, which could be hazardous to the operator. Autocleaning eliminated these problems and represents a significant advance over the prior manual techniques. However, with the implementation of autocleaning, there is no operator to visually inspect for buildup regularly, and wafers may continue to be processed even after unwanted deposits form on the cup, leading to the loss of these valuable wafers. Although an operator may periodically come in to inspect the plating apparatus, the operator has a limited ability to check for buildup due to time constraints and other various factors. Thus, a visual inspection may only occur once or twice per day, for example. By the time a visual inspection occurs, many valuable wafers may have already been processed under cup-bottom-plated conditions, resulting in the loss (or low yield) of these expensive wafers. In light of this difficulty, automated detection and cleaning of unwanted deposits is particularly valuable.

While autocleaning is advantageous for the reasons described herein, it can be difficult to determine the optimal timing/frequency for cleaning. For instance, throughput can suffer if cleaning happens too often because an electroplating cell is not available to process substrates while it is being cleaned. On the other hand, if cleaning does not occur frequently enough, many valuable wafers can be processed under poor conditions, leading to the loss or low yield of such wafers. As such, it is beneficial to detect the presence of unwanted plating on the electroplating apparatus. In this way, the decision regarding whether and when to clean the wafer holder can be based directly on the cleanliness of the wafer holder. Similarly, the detection methods described herein can be performed after a cleaning operation to confirm that the cleaning operation was successful.

Methods and Apparatus for Detecting Unwanted Metal Deposits on Substrate Holder

Certain embodiments herein provide methods of detecting whether and to what degree residual metal deposits are present on a substrate holder. These methods may be practiced at the same time as, or immediately before, or immediately following, a cleaning operation, though they may be performed at any time when plating is not occurring. In certain cases the detection methods are practiced each time an autocleaning process occurs (e.g., before a cleaning process to trigger the cleaning process, and/or after a cleaning process to confirm that the cleaning process was successful). In other cases the detection methods are practiced more or less frequently. For example, detection may occur after each wafer is processed, after a certain number of wafers are processed, after a certain amount of charge (measured in coulombs, for example) has been transferred during electrodeposition processes, or after a certain total amount or thickness of film has been deposited during electrodeposition processes.

Figure 2A:
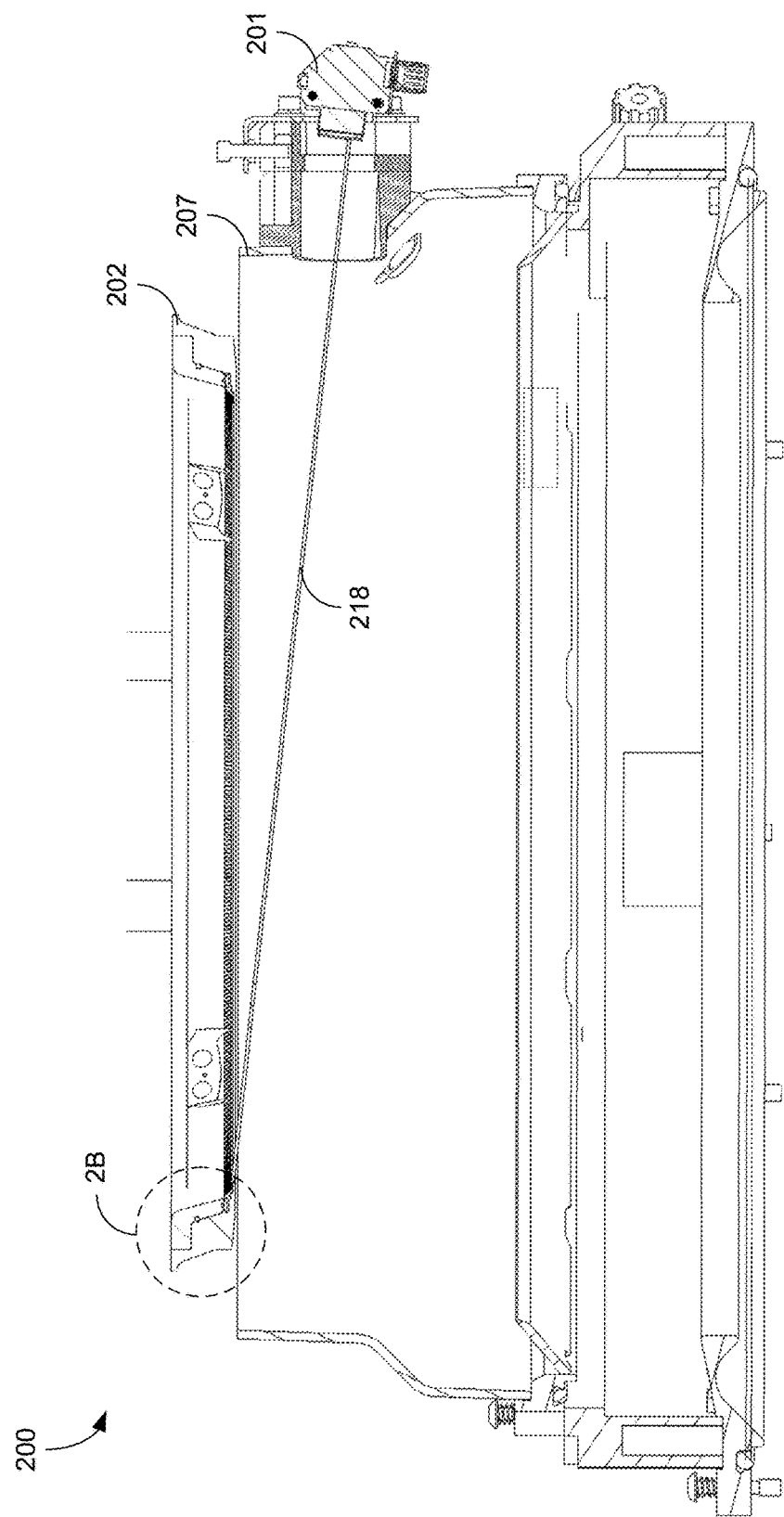
FIG. 2A shows a simplified view of a portion of an electroplating apparatus having a plating sensor installed thereon.
Figure 2B:
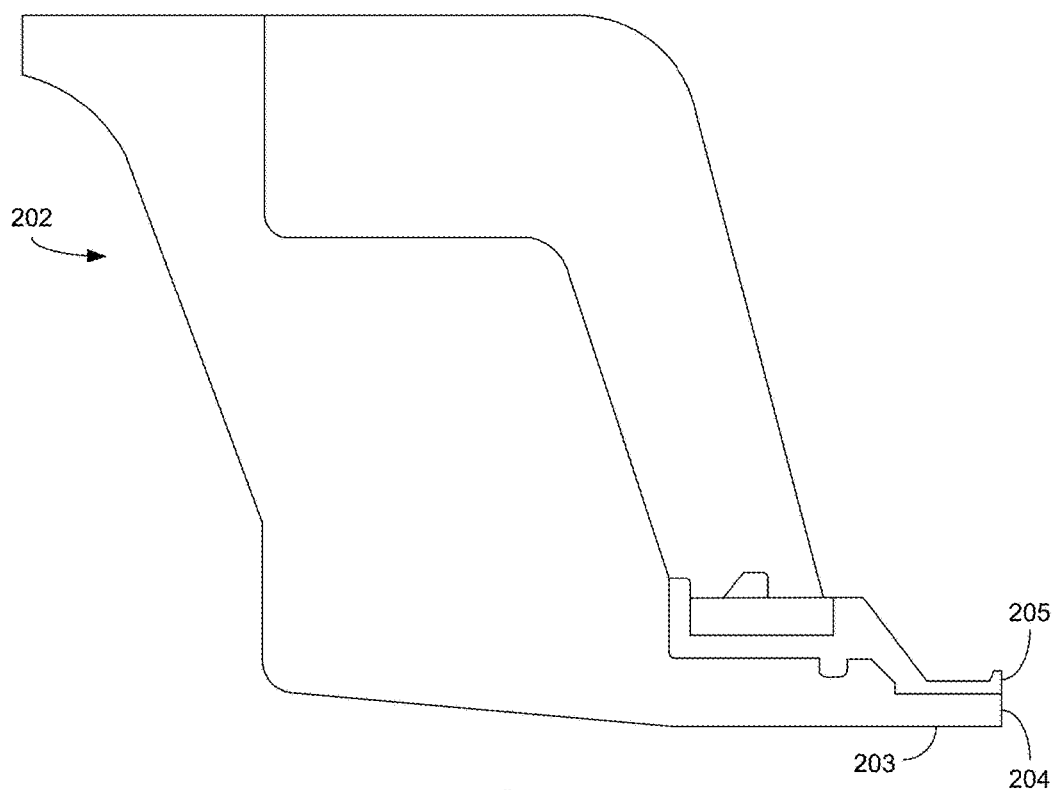
FIG. 2B depicts a close-up cross-sectional view of a substrate holder.
Figure 2C:
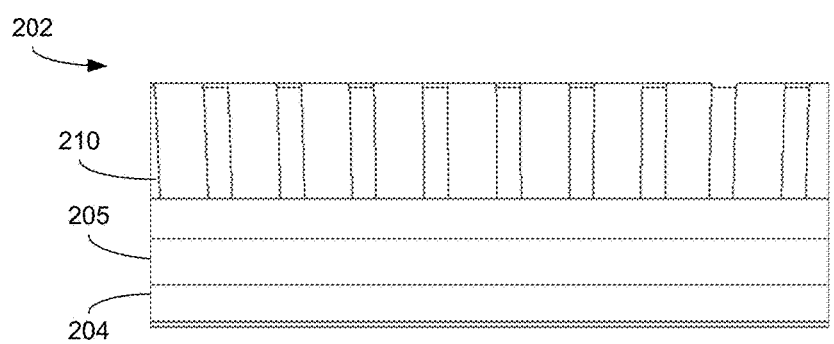
FIG. 2C depicts a close-up front view of the substrate holder in FIG. 2B.

FIG. 2A shows a top portion of an electroplating cell 200 with a plating sensor 201 installed thereon. FIG. 2B shows a close-up cross-sectional view of the cup 202 shown in FIG. 2A, which includes a bottom surface 203, an inner wall 204, and a lip seal 205. In FIG. 2A, the dotted circle labeled 2B highlights the portion of the apparatus depicted in FIG. 2B. FIG. 2C shows a close up front view of the cup 202, illustrating electrical contacts 210. During electroplating, a wafer is supported in the cup 202 in a face-down orientation. The position of the cup 202 is controlled by a lift mechanism that raises and lowers the cup 202 and substrate with respect to the electrolyte contained in the electroplating cell 200. The electroplating cell 200 includes a drip shield 207, which is open on the top and bottom. After a wafer is loaded into the cup 202, the lift mechanism lowers the cup 202 through the drip shield 207 before immersing the wafer in electrolyte. In this example, the plating sensor 201 is installed on a wall of the drip shield 27. The line of sight for the plating sensor 201 is labeled 218.

This positioning is advantageous for a number of reasons. For instance, because the plating sensor 201 is installed on the drip shield 207, it is shielded from the plating chemistry. Such chemistry can affect the optics of optical sensors, leading to poor quality (e.g., not repeatable) measurements. Moreover, exposure to such chemistry can shorten the lifespan of the sensor. As such, by removing the plating sensor 201 from the proximity of the plating chemistry, these chemistry-related problems can be minimized or avoided. In some cases, the drip shield 207 may provide a temporary or permanent physical barrier between the plating sensor 201 and the plating chemistry. For a temporary physical barrier, a shutter may be used. The shutter may remain closed while electroplating is occurring, and at other times when the plating sensor is not in use. For a permanent physical barrier, the drip shield 207 may include a window through which the plating sensor 201 measures. In some other cases, the drip shield 207 may include a cutout through which the plating sensor 201 measures, where the cutout does not provide any physical barrier between the plating sensor 201 and plating chemistry. The distance provided between the plating sensor 201 and plating chemistry may be sufficient to achieve the advantages described above, though the use of a physical barrier/window may strengthen these advantages.

Certain additional steps may be taken in some embodiments to reduce the likelihood of contaminating the plating sensor with plating chemistry. In some cases, gas may be flowed over the plating sensor during times when contamination is more likely (e.g., when detection is occurring, or when the substrate holder raised from the plating position). In these or other cases, the plating sensor (or a portion thereof, e.g., a lens) may include a hydrophobic and/or oxidation resistant coating. These steps may further protect the plating sensor, extending its useful lifetime.

Another advantage to placing the plating sensor 201 on the drip shield 207 is that this placement achieves a relatively deep depth of focus for the plating sensor 201, as compared to a plating sensor that is placed in close proximity to the deposits it detects (e.g., a plating detector that detects unwanted deposits on the bottom surface of a cup from a short distance under the cup, or a plating detector positioned on a swing arm that detects unwanted deposits anywhere on the cup from a short distance away, as described in U.S. patent application Ser. No. 14/178,804, filed Feb. 12, 2014, and incorporated by reference above). As shown in FIG. 2A, the plating sensor 201 detects deposits positioned across the electroplating cell, opposite the plating sensor 201. The relatively large diameter of the electroplating cell results in a relatively large depth of focus for the plating sensor 201. A deeper depth of focus increases quality of measurements (e.g., more repeatable) by reducing signal loss due to eccentricity of the wafer holding apparatus. In some cases, the plating sensor 201 may be positioned on another portion of the apparatus, such that it resides in a similar position as shown in FIG. 2A. The drip shield itself is not necessary, but provides a convenient point of attachment for the plating sensor in certain embodiments.

In certain cases, the distance between the plating sensor and the region that it senses (often on the lip seal opposite the plating sensor, as described further below) is at least about 200 mm, or at least about 250 mm, or at least about 300 mm, or at least about 400 mm, or at least about 450 mm. This distance may roughly correspond with the diameter of the wafer being electroplated. In many cases where the substrate is plated in a horizontal orientation, the plating sensor senses across the diameter of the electroplating cell such that the sensor beam is substantially more horizontal than vertical (e.g., within about 30 degrees of horizontal).

A number of different types of plating sensors may be used. Example plating sensors include, but are not limited to, color-based sensors, intensity-based sensors, vision-based camera/sensors (which may be used in combination with image recognition/classification methods to detect unwanted deposits), and any combination thereof. The plating sensor may be digital, analog, or some combination thereof. In a particular example, the plating sensor includes (1) optics for illuminating the sensor target area, and (2) optics for collecting a signal from the illuminated sensor target area.

The optics for illuminating the sensor target area typically include a light source such as a light emitting diode (LED), a laser diode, lamp, etc. In some cases, a fiber optic cable may be used to direct light from the light source onto the sensor target area. The optics for collecting a signal from the illuminated sensor target area typically includes an optical sensor. The optical sensor may generate electricity when illuminated, for example where the optical sensor is a photovoltaic or photo-emissive sensor. In other cases, the optical sensor may change an electrical property when illuminated, for example where the optical sensor is a photo-resistor, photo-conductor, etc. General examples of optical sensors include, but are not limited to, photoelectric, photo diodes, photoresistors, photoconductors, proximity light sensors, photovoltaic light sensors, photoemissive light sensors, etc.

The area at which the plating sensor is aimed may be referred to as the sensor target area. In various embodiments, the sensor target area is an area on the lip seal and/or an area on the inner wall of the cup (e.g., inner wall 204 of FIG. 2A). The sensor target area may be designed to provide a signal that contrasts with the signal provided by an unwanted metal deposit, as discussed further below.

The optics for illuminating the sensor target area and the optics for collecting the signal from the sensor target area may be combined in a single element, or they may be provided separately from one another. In the examples shown in FIGS. 2A, 3A, 4D, 6A, and 6B, the illumination and collection optics are provided together in the plating sensor (elements 201, 301, 401, and 601). In some other cases, the plating sensors shown in the figures may include the collection optics, while the illumination optics are provided elsewhere (e.g., anywhere having a line of sight to the sensor target area). It is advantageous to have the collection optics (and in some cases the illumination optics) positioned relatively far away from the sensor target area for the reasons described above.

In one embodiment, the plating sensor is a small spot size contrast sensor. Such sensors differentiate between areas of the apparatus where unwanted plating is present vs. absent based on the signal strength received when illuminating each area of the apparatus. In one example, the sensor target area on the lip seal and/or inner wall of the cup may be white (or a light color) such that it provides a relatively strong signal to the contrast sensor when illuminated. By contrast, unwanted metal deposits tend to be dark and provide a relatively weaker signal to the contrast sensor when illuminated. A threshold signal can be identified to distinguish between areas where unwanted metal deposits are present vs. areas where unwanted deposits are absent.

Drying the Sensor Target Area

After electroplating on substrates, it is common for moisture to persist on the lip seal and cup of the substrate holder for approximately 30 minutes. This moisture can affect the quality/repeatability of measurements. In order to obtain high quality measurements without waiting for the apparatus to dry, a dryer can be provided to quickly remove moisture from the sensor target area (and any other areas that need drying). The dryer may be incorporated into a cleaning assembly (e.g., on a cleaning arm that swings into place to clean the lip seal/cup), or provided on a separate mechanism (which may be provided on a swing arm similar to the cleaning arm, or on another piece of hardware). In various embodiments, the dryer includes a nozzle and supply line for delivering gas (e.g., $N_2$, inert gas, air, etc.) toward the sensor target area. In some cases, the dryer may dry the bottom of the cup in addition to the lip seal and/or inner wall of the cup.

Figure 3A:
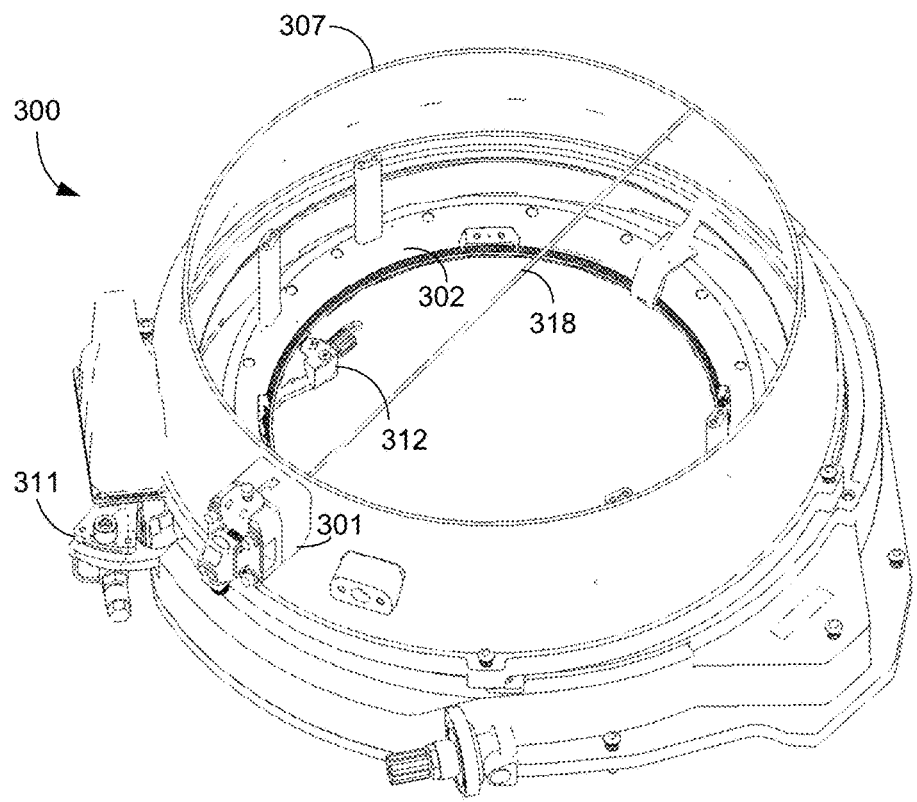
FIG. 3A illustrates a portion of an electroplating apparatus having a plating sensor and cleaning arm installed thereon, where the cleaning arm includes a dryer.

FIG. 3A illustrates a portion of an electroplating cell 300 having a plating sensor 301 installed on a drip shield 307, where a dryer 313 is incorporated into a cleaning assembly 311. The line of sight for the plating sensor 301 is labeled 318. In FIG. 3A, the cup 302 is shown in the cleaning position (e.g., lowered within the drip shield 307, above the electrolyte such that the cleaning arm can travel under the cup 302 without dipping into the electrolyte), which may be the same as the drying position. The cleaning assembly 311 includes a swing arm 312, which is shown more clearly in FIG. 3B. In this example, the swing arm 312 of the cleaning assembly 311 includes a cleaning head 314, a gas line 315, and a nozzle 316. The gas line 315 and nozzle 316 form the dryer 313. Additional fluid lines and nozzles may be provided on the swing arm 312 to deliver cleaning fluid in some cases. In a similar example, the cleaning head 314 is provided on a first swing arm, and the dryer 313 is provided on a second swing arm (not shown). The swing arm(s) may move relative to the cup to thereby allow the swing arm to clean and/or dry along the entire cup. In one embodiment, the cup rotates while the swing arm(s) remain stationary. In another embodiment, the cup remains stationary while the swing arm(s) rotate to bring them around the entire cup. In another embodiment, a combination of these movements is used.

In some cases, drying the sensor target area can have a deleterious effect on subsequent plating processes performed on wafers. In such cases, the first wafer that is plated after drying/detection may suffer "first wafer" effects that result in substantial non-uniformities compared with subsequently processed wafers. The subsequently processed wafers experience different plating conditions compared to the first wafer because the relevant areas of the apparatus become re-wet during processing of the first wafer. The first wafer effects can be eliminated by simply re-wetting the sensor target area (and any other areas that need wetting) prior to processing the first wafer after a detection operation. The cleaning assembly may be used to rewet the apparatus in some cases. In other cases, a separate fluid line/nozzle may be provided for this purpose.

Alignment of the Plating Sensor

The plating sensor may be aligned such that it is focused on the sensor target area before detection. The plating sensor may be aligned a first time when it is installed, and then re-aligned each time it is used. The initial alignment may be done to position the plating sensor on the drip shield, and the subsequent alignments may be done to position the substrate holder lift mechanism such that the sensor target area is aligned with the plating sensor.

In a particular example, the plating sensor may be installed on the drip shield using adjustable mounting hardware that allows for relative movement between the plating sensor and the drip shield. Examples of such hardware include screws, rods, snaps, fasteners, etc. In one embodiment, the plating sensor is mounted on the drip shield using one or more screws that control the relative vertical position of the plating sensor on the drip shield. By turning the screw one way or another, the plating sensor moves up or down on the drip shield. In these or other embodiments, the plating sensor may be mounted on the drip shield using one or more screws that control the relative horizontal/circumferential position of the plating sensor on the drip shield. By turning the screw one way or another, the plating sensor moves left or right around the drip shield. Any adjustable attachment hardware may be used. The plating sensor may be positioned to sense through a cutout or window in the drip shield. After the plating sensor is appropriately positioned on the drip shield, an alternative piece of hardware (e.g., the lift mechanism that controls the position of the substrate holder) may be used to align the plating sensor to the sensor target area each time these elements need to be aligned during processing.

As mentioned above, in some cases the sensor target area is an area on the lip seal and/or an area on the inner wall of the cup. In a particular embodiment the sensor target area is on the lip seal, and has a height that is comparable to, or smaller than, the height of the lip seal. In another embodiment, the sensor target area is on the inner wall of the cup, and has a height that is comparable to, or smaller than, the height of the inner wall of the cup. In yet another embodiment, the sensor target area is on both the lip seal and inner wall of the cup, and has a height that is comparable to or less than the combined height of the lip seal and inner wall of the cup. The use of a small sensor target area minimizes background noise in the collected data.

Figure 4A:
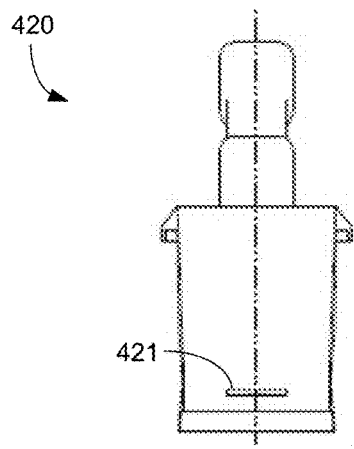
FIG. 4A shows a front view.
Figure 4B:
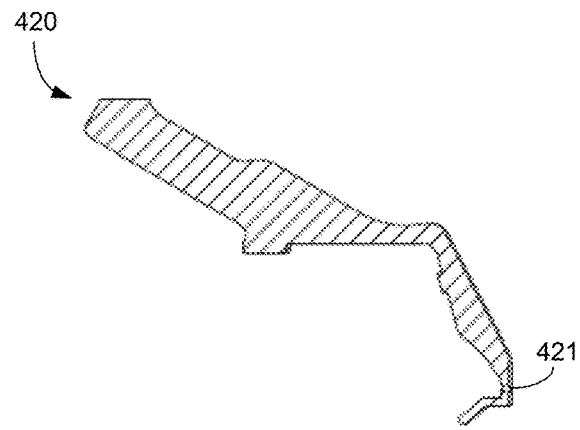
FIG. 4B shows a side view of an alignment fixture that may be used in combination with a plating sensor according to certain embodiments.
Figure 4C:
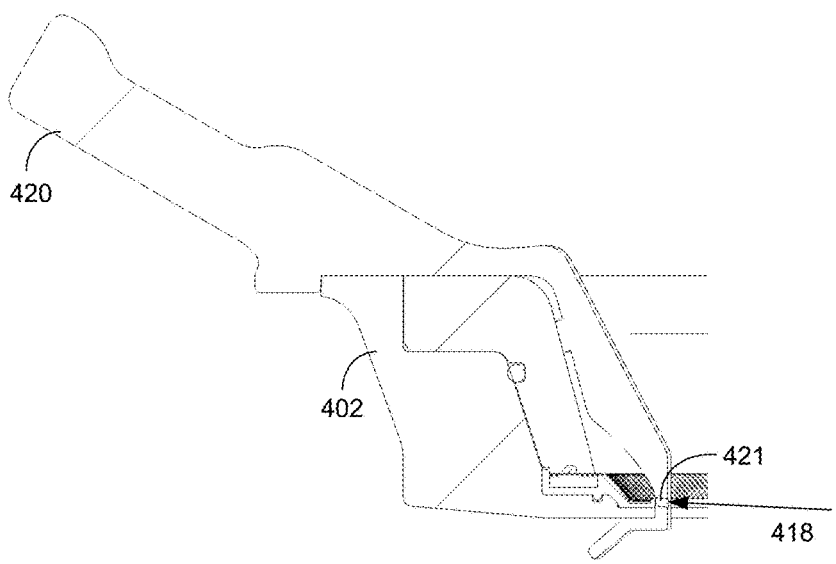
FIG. 4C illustrates a side view of the alignment fixture shown in FIGS. 4A and 4B installed over a cup of a substrate holder.
Figure 4D:
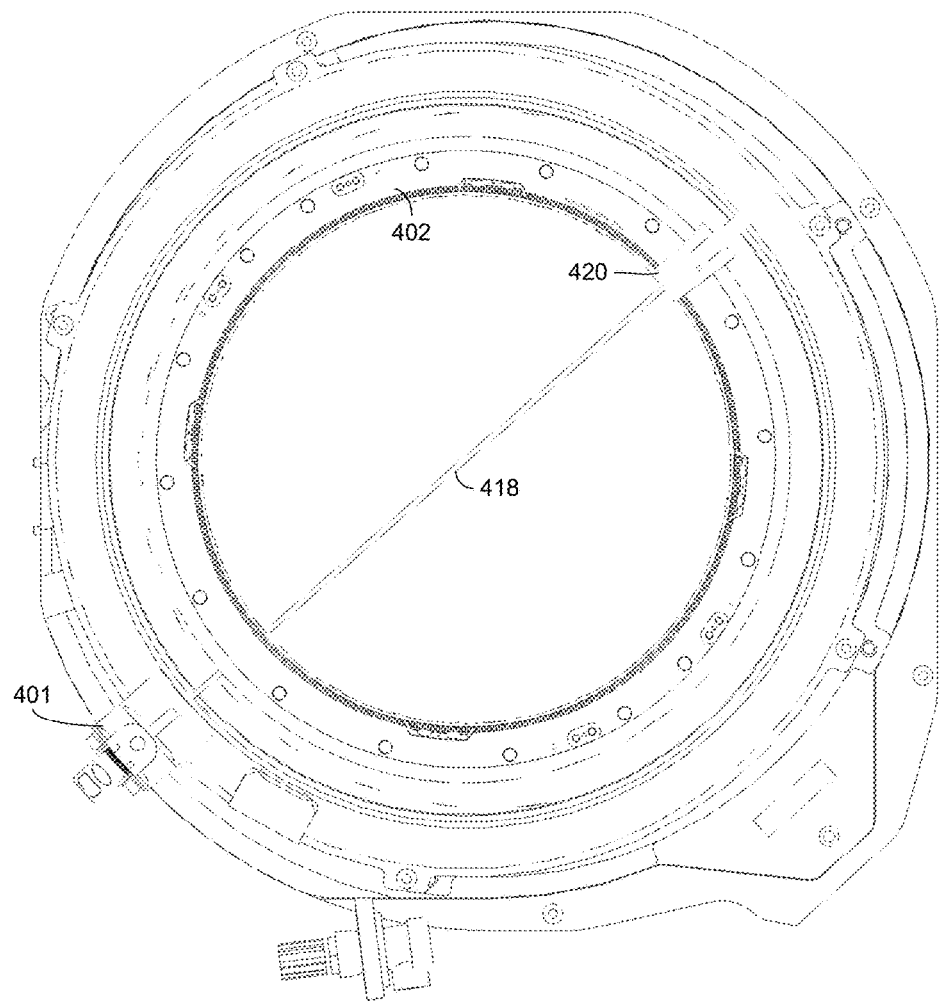
FIG. 4D is a top-down view of a portion of an electroplating apparatus illustrating a plating sensor aligned with the alignment fixture shown in FIGS. 4A-4C.

FIGS. 4A-4D depict an alignment fixture 420 having a cutout 421. FIG. 4A shows a front view of the alignment fixture 420, FIG. 4B shows a side view of the alignment fixture 420, FIG. 4C depicts a side view of the alignment fixture 420 installed on a cup 402, and FIG. 4D shows a top view of the alignment fixture 420 installed on cup 402, opposite plating sensor 401. The line of sight for the plating sensor 401 is labeled 418. The alignment fixture 420 is positioned on the cup 402 such that the cutout 421 is aligned with the line of sight 418 from the plating sensor 401, as shown in FIG. 4C. The position of the cutout 421 determines the position of the sensor target area. For example, if it is desired that the sensor target area is on the lip seal of the cup 402, the cutout 421 may be positioned relatively higher, and if it is desired that the sensor target area is on the inner wall of the cup 402, the cutout 421 may be positioned relatively lower (because the inner wall of the cup is below the lip seal of the cup).

In one example, the alignment fixture may be fixedly mounted to the cup such that the alignment fixture and cup do not move relative to one another. In such cases, the alignment fixture may be used to align the plating sensor and the sensor target area at an initial stage of each detection process. After this initial alignment, the lift mechanism for the substrate holder assembly maintains the cup at the desired alignment height while the cup is rotated. This rotation allows the plating sensor to detect along the entire lip seal and/or inner wall of the cup. As the cup rotates, the alignment fixture rotates with it. In another example, the alignment fixture may be mounted over the cup such that the cup moves relative to the alignment fixture. For instance, the cup may rotate/slide under the alignment fixture. In such cases, the alignment fixture may remain aligned with the line of sight of the plating sensor throughout the entire detection process, while the cup rotates under the alignment fixture such that the entire lip seal and/or inner wall of the cup can be evaluated by the plating sensor. In various embodiments, the alignment fixture may be removably mounted over the cup. The alignment fixture may be mounted and removed as needed. For example, the alignment fixture may be mounted on the cup after the apparatus is used to electroplate on one or more substrates. The alignment fixture may remain mounted until the substrate holder/sensor target area are aligned with the plating sensor, or until after the detection is complete. At this point, the alignment fixture may be removed. The installation and removal of the alignment fixture can be repeated as needed as additional substrates are processed. By removably mounting the alignment fixture, it can be ensured that the alignment fixture does not interfere with the electroplating process.

The alignment fixture may be designed such that its front face provides strong contrasting signals depending on which portion of the alignment fixture is aligned with the plating sensor. This contrast may include differences in absorption, reflection, scattering etc. A first signal is generated when the alignment fixture/substrate holder/sensor target area are properly aligned with the plating sensor, and a second signal that contrasts with the first signal is generated when the alignment fixture/substrate holder/sensor target area are misaligned with the plating sensor. In one example, the alignment fixture includes a first portion (e.g., having a height equal or less than the sensor target area) that is positioned in the line of sight between the plating sensor and the sensor target area when the alignment fixture is installed, and a second portion positioned vertically above and/or below the first portion (in some cases surrounding the first portion), where the first and second portions contrast with one another with respect to a property measured by the plating sensor. For instance, the first portion may be white and the second portion may be black (any sets of differentiable colors/properties may be used). Alternatively, the first portion of the alignment fixture may be a cutout that allows the plating sensor to sense a property directly on the sensor target area. In one example where the first portion of the alignment fixture is a cutout, the sensor target area (e.g., lip seal and/or inner wall of cup) is white, while the front face of the alignment fixture is black. Other contrasting combinations of colors/properties may be used, as well. With respect to FIGS. 4A-4C, the first portion may be cutout 421, and the second portion may be the remaining areas of the front face of the alignment fixture 420. In a similar example, cutout 421 may be replaced with an area (e.g., a white area) that contrasts with the remaining areas of the front face of the alignment fixture. Generally speaking, the signal indicating that the alignment fixture/substrate holder/sensor target area are aligned with the plating sensor may be a signal from a surface of the alignment fixture, or from a surface of the sensor target area.

In order to align the sensor target area with the plating sensor, the plating sensor takes a series of measurements as the cup is moved through different vertical positions. In some cases this may be done automatically. The cup may be moved using the lift mechanism that controls the vertical position of the substrate holder assembly. The alignment position is then set based on the maximum (or minimum) intensity of signal received. At this position, the line of sight of the plating sensor is aligned with the first portion of the alignment fixture, which indicates that the plating sensor is also vertically aligned with the sensor target area. This example assumes that the plating sensor is a contrast sensor, though a similar alignment method may be used for other types of sensors. In a similar embodiment, the cup may remain stationary, and the position of the plating sensor may be adjusted to align its line of sight with the first portion of the alignment fixture.

The alignment fixture may be made of a number of different materials. In a number of cases, the alignment fixture may be made of a thermoplastic material. Example materials include, but are not limited to, polycarbonate, acrylonitrile butadiene styrene (ABS), polypropylene, polyvinylidene fluoride (PVDF), polytetrafluoroethylene (PTFE), polyethylene terephthalate (PET), polyphenylene sulfide (PPS), polyphenylsulfone (PPSF), fluoroelastomers (FKM elastomers), and blends/alloys/bonded assemblies of these materials. ABS materials come in a number of varieties including ABS-M30 (which is stronger than standard ABS), ABS-ESDI (acrylonitrile butadiene styrene-static-dissipative, which is an electrostatic-dissipative material), etc. Other example thermoplastic materials include Ultem 9085, polycarbonate ISO, polycarbonate-ABS blends, etc. In a number of embodiments, the alignment fixture may be manufactured through three dimensional printing techniques. These techniques may involve preparing a computer-based three dimensional model of the alignment model, heating a printing material (e.g., any of the thermoplastic materials mentioned above) to an elevated temperature, and dispensing the heated printing material to form the alignment fixture according to the three dimensional model.

Example Flowchart

Figure 5:
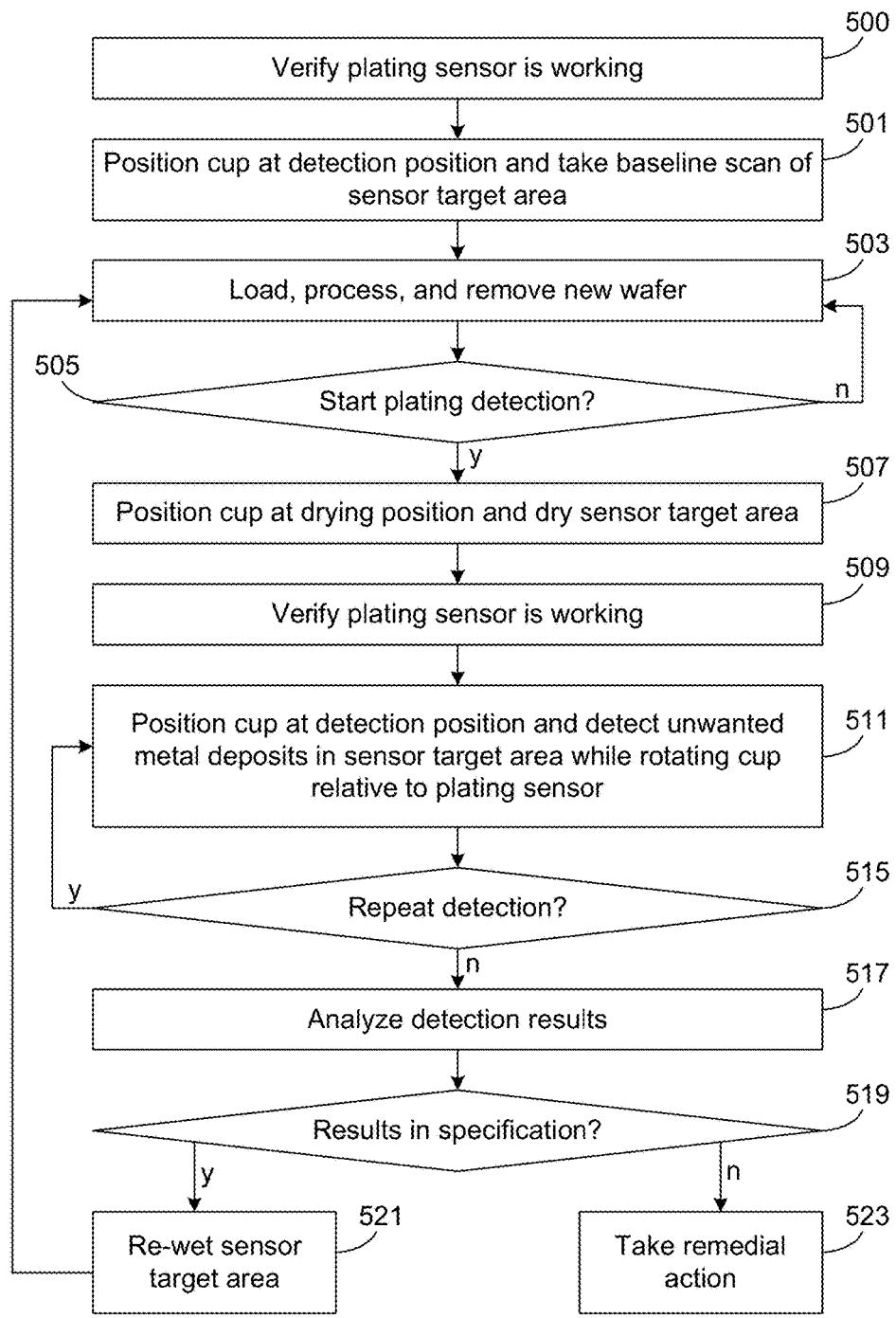
FIG. 5 is a flow chart describing a method of detecting the presence or absence of unwanted metal deposits on a substrate holder according to certain embodiments.

FIG. 5 is a flowchart depicting a method of processing substrates while periodically or intermittently detecting the presence or absence of unwanted metal deposits on the substrate holder. The method begins with operation 500, where the plating sensor is verified to be working. The verification may involve moving the substrate holder with respect to the plating sensor such that the plating sensor receives two distinguishable signals. These distinguishable signals ensure that the plating sensor is properly connected and functioning normally. In cases where the sensor is only able to detect one signal level, it may indicate that a sensor cable is not properly connected, or that the plating sensor is not functioning normally.

FIGS. 6A and 6B illustrate a portion of an electroplating apparatus in two positions that may be used during verification in operation 500 of FIG. 5. The electroplating apparatus includes a drip shield 607 with a plating sensor 601 installed thereon. The line of sight of the plating sensor 601 is labeled 618. In FIG. 6A, the cup 602 and the plating sensor 601 are in a first relative position, where the line of sight of the plating sensor 601 passes under the cup 602. In FIG. 6B, the cup 602 and the plating sensor 601 are in a second relative position, where the line of sight of the plating sensor 601 impinges upon the sensor target area on the cup (e.g., on the lip seal and/or on the inner wall of the cup). The plating sensor 601 should measure distinguishable signals at the two positions shown in FIGS. 6A and 6B. In one example where the plating sensor is a digital contrast sensor, the sensor output reads "on" in the first relative position of FIG. 6A, and "off" in the second relative position of FIG. 6B (or vice versa).

In some cases where the apparatus includes an alignment fixture as described in relation to FIGS. 4A-4D, the verification in operation 500 of FIG. 5 may be done by moving the cup/alignment fixture relative to the plating sensor such that (1) at a first relative position, the line of sight of the plating sensor passes through the cutout on the alignment fixture to impinge upon the sensor target area, and (2) at a second relative position, the line of sight of the plating sensor either impinges upon the front face of the alignment fixture in a region other than the cutout, or passes under the cup as shown in FIG. 6A. In this way, it can be verified that the plating sensor and the sensor target area are properly aligned and functioning. If the plating sensor is not able to detect a difference between the signal received at the first and second relative positions, this indicates that the plating sensor is malfunctioning and should be inspected, repaired, or replaced.

After the verification in operation 500, the cup is positioned at a detection position and the plating sensor takes a baseline scan by scanning the sensor target area through one full rotation in operation 501. In cases where an alignment fixture is used, for example as described in FIGS. 4A-4D, positioning the cup at the detection position may involve the alignment processes described above. For example, the cup may be moved to a position that achieves a maximum signal at the plating sensor, indicating that the plating sensor's line of sight is aligned with the cutout on the alignment fixture (and is therefore aligned with the sensor target area on the lip seal and/or inner wall of the cup).

In many cases, the plating sensor is mounted on the drip shield and remains substantially stationary during measurement. In such cases, the substrate holder may rotate such that the plating sensor can scan along the entire length of the sensor target area (e.g., along the entire lip seal and/or inner wall of the cup). In some other cases, the plating sensor may move while the substrate holder remains stationary to allow for the entire sensor target area to be scanned. The baseline scan may be useful for comparing against future scans. Operation 501 may be performed intermittently, for example when a new lip seal or cup is installed.

Figure 3B:
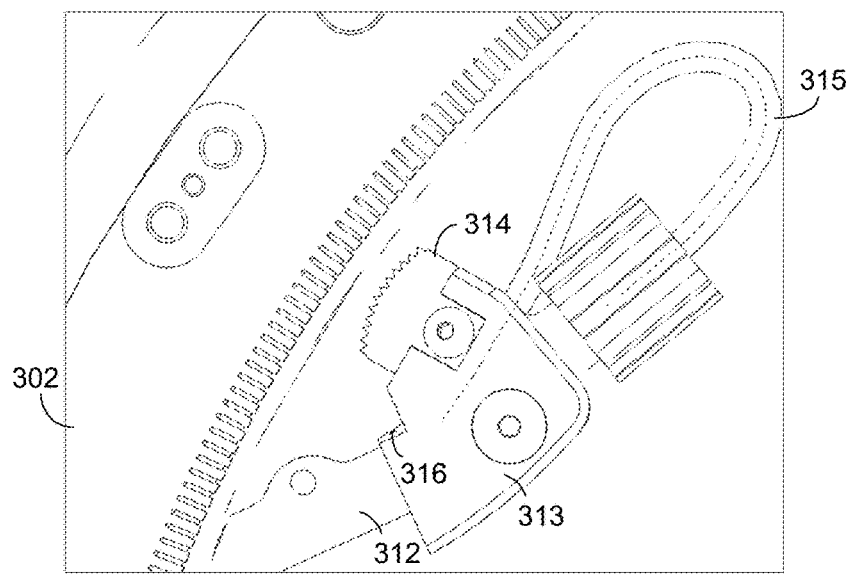
FIG. 3B shows a close-up view of the cleaning arm and dryer shown in FIG. 3A.

At operation 503, a new wafer is loaded, processed, and then removed from the electroplating cell of the electroplating apparatus. At operation 505, it is determined whether to start detection of unwanted metal deposits. In cases where no detection is desired at operation 505, the method may repeat with operation 503, where additional wafers are loaded, processed, and then removed. In cases where detection is desired at operation 505, the method continues at operation 507, where the cup is positioned at a drying position and the sensor target area is dried. The lift mechanism controlling the vertical position of the substrate holder assembly may be used to control the position of the cup. FIGS. 3A and 3B illustrate the cup 302 in the drying position according to one embodiment. In these examples, the cup 302 is within or below the drip shield 307 when in the drying position. The cup 302 is positioned sufficiently high to allow the swing arm 312 to pass under it. The swing arm 312 includes the dryer 313 for drying the sensor target area. The dryer 313 may deliver a gas stream (e.g., $N_2$, inert gas, air, etc.) toward the sensor target area to dry this area. The cup 302 rotates relative to the dryer 313 such that the entire length/circumference of the sensor target area can be dried.

Returning to FIG. 5, the method continues at operation 509, where the plating sensor is verified to be working. The verification at operation 509 is similar to the verification at operation 500, and for the sake of brevity the description will not be repeated. Next, at operation 511, the cup is positioned at a detection position and then rotated with respect to the plating sensor while the plating sensor is used to detect the presence or absence of unwanted metal deposits in the sensor target area. Positioning the cup in the detection position in operation 511 is similar to positioning the cup in the detection position in operation 501, and for the sake of brevity the description will not be repeated. Similarly, the relative rotation between the plating sensor and the cup is similar in operations 511 and 500, and the description will not be repeated. The detection in operation 511 is analogous to the baseline scan detection in operation 501, except that there may be unwanted metal deposits present. The plating sensor distinguishes between areas where unwanted plating is present and areas where unwanted plating is absent based on the signal received from each area.

At operation 515, it is determined whether the detection should be repeated. In some cases, it may be beneficial to confirm the detection results by running a second scan. If repeat detection is desired, the method repeats starting with operation 511. If no repeat detection is desired, the method continues with operation 517, where the detection results are analyzed. In some cases, the data from the plating sensor may be analyzed to determine (1) the length of each unwanted metal deposit and/or the length of the longest unwanted metal deposit, and/or (2) the percentage of the sensor target area that is covered with unwanted metal deposit. These values may be compared to a specification in operation 519. The specification may set a threshold for an acceptable amount of unwanted plating (e.g., deposits under a certain length may be acceptable, and/or sensor target areas that are plated under a certain percentage may be acceptable). These thresholds are specific to each application and may be determined empirically in some cases. In one example, the threshold maximum deposit length is about 0.5 cm, or about 1 cm (with deposits greater than this length being out of specification). In these or other examples, the threshold percentage of the sensor target area that is plated may be about 10%, or about 20% (with percentages greater than these values being out of specification).

In cases where the results are not within the specification in operation 519, it means that there is too much unwanted metal deposited on the sensor target area (e.g., on the lip seal and/or inner wall of the cup). In such cases, the method may continue with operation 523, where some remedial action is taken. Various possible remedial actions include, but are not limited to (1) sounding an alarm or otherwise alerting an operator, (2) taking the relevant electroplating cell offline and temporarily preventing further wafers from being processed therein, (3) rerouting wafers to other available electroplating cells, (4) performing a targeted clean of a portion of lip seal and/or inner wall of the cup (e.g., using either a manual or auto-cleaning method), (5) performing a full clean of the entire lip seal and/or inner wall of the cup (e.g., using either a manual or auto-cleaning method), (6) rescanning the sensor target area to confirm that a targeted or full clean was successful, (7) replace lip seal and/or cup, if needed, and (8) flag and/or inspect suspect wafers that were processed immediately before detection of unwanted metal deposits.

In cases where the results are within specification in operation 519, the detection results indicate that the sensor target area (e.g., lip seal and/or inner wall of the cup) is still sufficiently clean. In such cases, the method may continue with operation 521, where the sensor target area (and any other relevant portions of the apparatus) are re-wet. This re-wetting may be accomplished by delivering fluid (e.g., water, deionized water, electrolyte, etc.) toward the lip seal and/or the inner wall of the cup. This re-wetting reduces or avoids the first wafer effects that arise from plating on an apparatus that includes portions that become wet through plating. After re-wetting the relevant portions of the apparatus, the method continues at operation 503 where a new wafer is loaded, processed, and then removed from the electroplating apparatus. The method can be repeated any number of times to process any number of substrates.

A number of the operations shown in FIG. 5 may be omitted in some embodiments. In one example, the detection method simply involves operations 511, 517, and 519. The remaining operations may be included or omitted in any combination. Such operations may improve the method, leading to more reliable results and improved electroplating conditions, but are not necessary for practicing the disclosed embodiments.

Figures 7A, 7B:
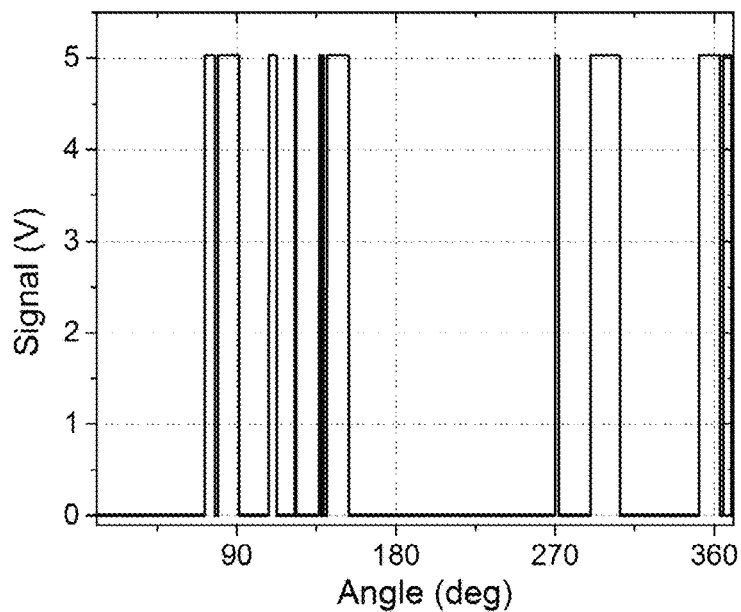
FIGS. 7A and 7B provide experimental results demonstrating that the methods described herein can be reliably used to detect the presence or absence (as well as the degree) of unwanted metal deposits on a substrate holder.

FIGS. 7A and 7B provide experimental results where a plating sensor was used to detect unwanted metal deposits on a cup of a substrate holder. In this example, the plating sensor was a digital contrast sensor. With respect to FIG. 7A, the graph depicts the signal received by the plating sensor at different angular positions on the substrate holder. In this example, the 5 V signal indicates the presence of unwanted metal deposits, and the 0 V signal indicates the absence of unwanted metal deposits. FIG. 7B shows a table illustrating the measurement results (percentage of sensor target area that is plated with unwanted metal deposits) for a particular electroplating apparatus that was scanned 10 times. No changes were made to the electroplating apparatus between the different scans. The scans were repeated to determine whether the measurement was reliable. As shown in FIG. 7B, the results were reliable, showing a standard deviation of only 0.15%. These results demonstrate that the disclosed methods may be used to reliably detect the presence/absence/degree of unwanted metal deposits on the sensor target area.

Data from the plating sensor, such as that shown in FIG. 7A, can be combined with information from a rotational axis encoder to correlate the plating sensor data with specific portions of the sensor target area. The rotational axis encoder converts an angular position (e.g., along the substrate/cup) to an analog or digital code, allowing a user to reliably designate a particular region of the substrate/substrate holder. By combining the plating sensor data with information from the rotational axis encoder, a user can determine exactly where the problem areas are on the cup. This location-specific data may be used to trigger a targeted cleaning of the affected area in some cases.

Moreover, the location-specific data may be correlated with wafer performance. In one example, the location-specific data is correlated with wafer uniformity data. Such correlations can be used to identify useful trends. In some cases, a first-principle model, machine learning algorithm, etc. is applied to the data in order to predict the useful lifetime of the lip seal and/or to predict when the lip seal should be maintained (e.g., cleaned, manually cleaned, replaced, etc.). These models may be applied to each electroplating cell in a multi-station electroplating apparatus such as those described below.

Apparatus

The methods described herein may be performed by any suitable apparatus. A suitable apparatus includes hardware for accomplishing the process operations and a system controller having instructions for controlling process operations in accordance with the present embodiments. For example, in some embodiments, the hardware may include one or more process stations included in a process tool.

Figure 8:
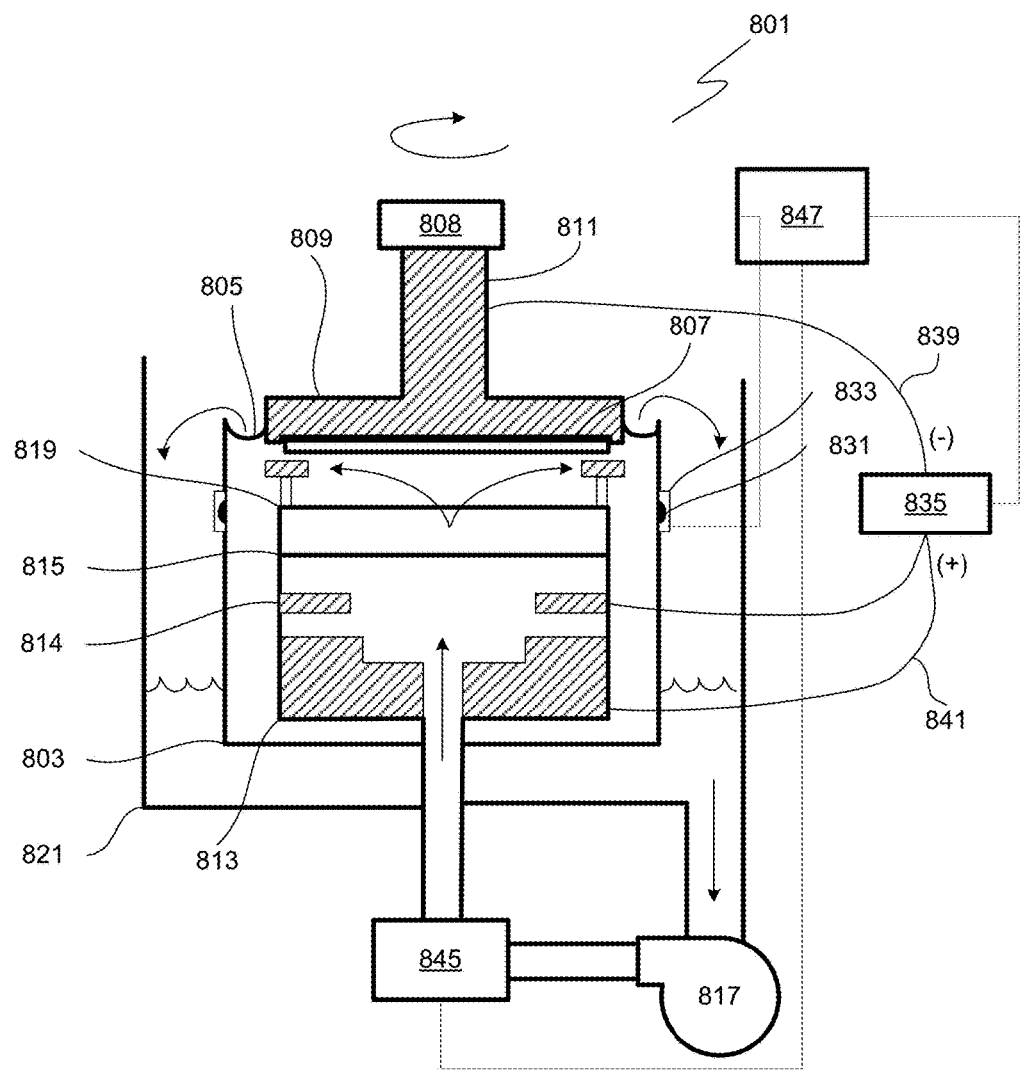
FIG. 8 shows a simplified view of an electroplating apparatus.

FIG. 8 presents an example of an electroplating cell in which electroplating may occur. FIG. 8 does not show the plating sensor described above, though it is understood that the apparatus shown in FIG. 8 can be modified to include such a plating sensor, for example on a drip shield that fits with/above plating bath 803. Often, an electroplating apparatus includes one or more electroplating cells in which the substrates (e.g., wafers) are processed. Only one electroplating cell is shown in FIG. 8 to preserve clarity. To optimize bottom-up electroplating, additives (e.g., accelerators, suppressors, and levelers) are added to the electrolyte; however, an electrolyte with additives may react with the anode in undesirable ways. Therefore anodic and cathodic regions of the plating cell are sometimes separated by a membrane so that plating solutions of different composition may be used in each region. Plating solution in the cathodic region is called catholyte; and in the anodic region, anolyte. A number of engineering designs can be used in order to introduce anolyte and catholyte into the plating apparatus.

Referring to FIG. 8, a diagrammatical cross-sectional view of an electroplating apparatus 801 in accordance with one embodiment is shown. The plating bath 803 contains the plating solution (having a composition as provided herein), which is shown at a level 805. The catholyte portion of this vessel is adapted for receiving substrates in a catholyte. A wafer 807 is immersed into the plating solution and is held by, e.g., a "clamshell" substrate holder 809, mounted on a rotatable spindle 811, which allows rotation of clamshell substrate holder 809 together with the wafer 807. A general description of a clamshell-type plating apparatus having aspects suitable for use with this invention is described in detail in U.S. Pat. No. 6,156,167 issued to Patton et al., and U.S. Pat. No. 6,800,187 issued to Reid et al., which are incorporated herein by reference in their entireties.

An anode 813 is disposed below the wafer within the plating bath 803 and is separated from the wafer region by a membrane 815, preferably an ion selective membrane. For example, Nafion™ cationic exchange membrane (CEM) may be used. The region below the anodic membrane is often referred to as an "anode chamber." The ion-selective anode membrane 815 allows ionic communication between the anodic and cathodic regions of the plating cell, while preventing the particles generated at the anode from entering the proximity of the wafer and contaminating it. The anode membrane is also useful in redistributing current flow during the plating process and thereby improving the plating uniformity. Detailed descriptions of suitable anodic membranes are provided in U.S. Pat. Nos. 6,126,798 and 6,569,299 issued to Reid et al., both incorporated herein by reference in their entireties. Ion exchange membranes, such as cationic exchange membranes, are especially suitable for these applications. These membranes are typically made of ionomeric materials, such as perfluorinated co-polymers containing sulfonic groups (e.g. Nafion™), sulfonated polyimides, and other materials known to those of skill in the art to be suitable for cation exchange. Selected examples of suitable Nafion™ membranes include N324 and N424 membranes available from Dupont de Nemours Co.

During plating the ions from the plating solution are deposited on the substrate. The metal ions must diffuse through the diffusion boundary layer and into the TSV hole or other feature. A typical way to assist the diffusion is through convection flow of the electroplating solution provided by the pump 817. Additionally, a vibration agitation or sonic agitation member may be used as well as wafer rotation. For example, a vibration transducer 808 may be attached to the clamshell substrate holder 809.

The plating solution is continuously provided to plating bath 803 by the pump 817. Generally, the plating solution flows upwards through an anode membrane 815 and a diffuser plate 819 to the center of wafer 807 and then radially outward and across wafer 807. The plating solution also may be provided into the anodic region of the bath from the side of the plating bath 803. The plating solution then overflows plating bath 803 to an overflow reservoir 821. The plating solution is then filtered (not shown) and returned to pump 817 completing the recirculation of the plating solution. In certain configurations of the plating cell, a distinct electrolyte is circulated through the portion of the plating cell in which the anode is contained while mixing with the main plating solution is prevented using sparingly permeable membranes or ion selective membranes.

A reference electrode 831 is located on the outside of the plating bath 803 in a separate chamber 833, which chamber is replenished by overflow from the main plating bath 803. Alternatively, in some embodiments the reference electrode is positioned as close to the substrate surface as possible, and the reference electrode chamber is connected via a capillary tube or by another method, to the side of the wafer substrate or directly under the wafer substrate. In some of the preferred embodiments, the apparatus further includes contact sense leads that connect to the wafer periphery and which are configured to sense the potential of the metal seed layer at the periphery of the wafer but do not carry any current to the wafer.

A reference electrode 831 is typically employed when electroplating at a controlled potential is desired. The reference electrode 831 may be one of a variety of commonly used types such as mercury/mercury sulfate, silver chloride, saturated calomel, or copper metal. A contact sense lead in direct contact with the wafer 807 may be used in some embodiments, in addition to the reference electrode, for more accurate potential measurement (not shown).

A DC power supply 835 can be used to control current flow to the wafer 807. The power supply 835 has a negative output lead 839 electrically connected to wafer 807 through one or more slip rings, brushes and contacts (not shown). The positive output lead 841 of power supply 835 is electrically connected to an anode 813 located in plating bath 803. The power supply 835, a reference electrode 831, and a contact sense lead (not shown) can be connected to a system controller 847, which allows, among other functions, modulation of current and potential provided to the elements of electroplating cell. For example, the controller may allow electroplating in potential-controlled and current-controlled regimes. The controller may include program instructions specifying current and voltage levels that need to be applied to various elements of the plating cell, as well as times at which these levels need to be changed. When forward current is applied, the power supply 835 biases the wafer 807 to have a negative potential relative to anode 813. This causes an electrical current to flow from anode 813 to the wafer 807, and an electrochemical reduction (e.g. $Cu^{2+}+2e^-=Cu^0$) occurs on the wafer surface (the cathode), which results in the deposition of the electrically conductive layer (e.g. copper) on the surfaces of the wafer. An inert anode 814 may be installed below the wafer 807 within the plating bath 803 and separated from the wafer region by the membrane 815.

The apparatus may also include a heater 845 for maintaining the temperature of the plating solution at a specific level. The plating solution may be used to transfer the heat to the other elements of the plating bath. For example, when a wafer 807 is loaded into the plating bath the heater 845 and the pump 817 may be turned on to circulate the plating solution through the electroplating apparatus 801, until the temperature throughout the apparatus becomes substantially uniform. In one embodiment the heater is connected to the system controller 847. The system controller 847 may be connected to a thermocouple to receive feedback of the plating solution temperature within the electroplating apparatus and determine the need for additional heating.

The controller will typically include one or more memory devices and one or more processors. The processor may include a CPU or computer, analog and/or digital input/output connections, stepper motor controller boards, etc. In certain embodiments, the controller controls all of the activities of the electroplating apparatus. Non-transitory machine-readable media containing instructions for controlling process operations in accordance with the present embodiments may be coupled to the system controller.

Typically there will be a user interface associated with controller 847. The user interface may include a display screen, graphical software displays of the apparatus and/or process conditions, and user input devices such as pointing devices, keyboards, touch screens, microphones, etc. The computer program code for controlling electroplating processes can be written in any conventional computer readable programming language: for example, assembly language, C, C++, Pascal, Fortran or others. Compiled object code or script is executed by the processor to perform the tasks identified in the program. One example of a plating apparatus that may be used according to the embodiments herein is the Lam Research Sabre tool. Electrodeposition can be performed in components that form a larger electrodeposition apparatus.

Figure 9:
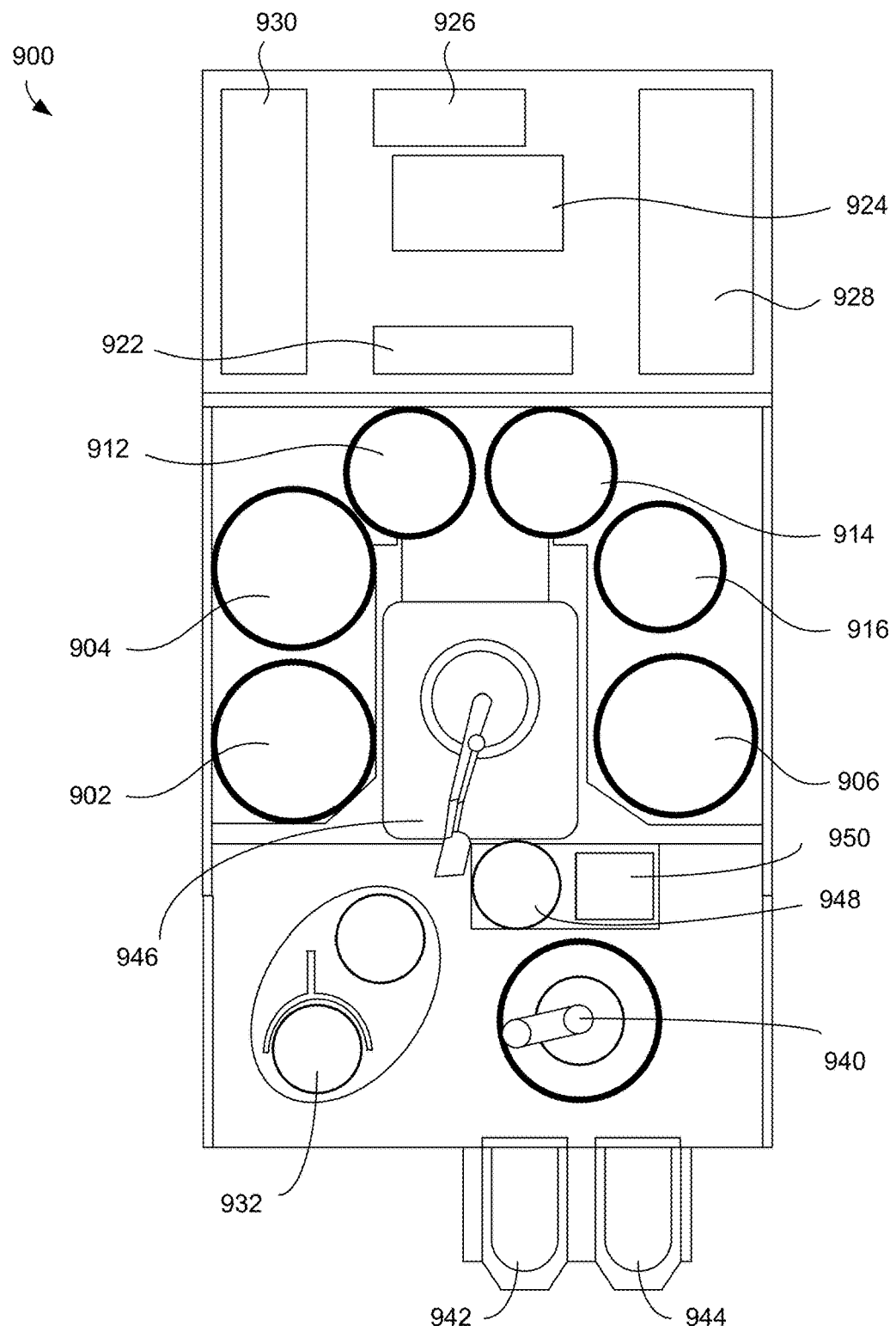
FIGS. 9 and 10 depict top down views of multi-station electroplating apparatuses.

FIG. 9 shows a schematic of a top view of an example electrodeposition apparatus. The electrodeposition apparatus 900 can include three separate electroplating modules 902, 904, and 906. The electrodeposition apparatus 900 can also include three separate modules 912, 914, and 916 configured for various process operations. For example, in some embodiments, one or more of modules 912, 914, and 916 may be a spin rinse drying (SRD) module. In other embodiments, one or more of the modules 912, 914, and 916 may be post-electrofill modules (PEMs), each configured to perform a function, such as edge bevel removal, backside etching, and acid cleaning of substrates after they have been processed by one of the electroplating modules 902, 904, and 906.

The electrodeposition apparatus 900 includes a central electrodeposition chamber 924. The central electrodeposition chamber 924 is a chamber that holds the chemical solution used as the electroplating solution in the electroplating modules 902, 904, and 906. The electrodeposition apparatus 900 also includes a dosing system 926 that may store and deliver additives for the electroplating solution. A chemical dilution module 922 may store and mix chemicals to be used as an etchant. A filtration and pumping unit 928 may filter the electroplating solution for the central electrodeposition chamber 924 and pump it to the electroplating modules.

A system controller 930 provides electronic and interface controls required to operate the electrodeposition apparatus 900. The system controller 930 (which may include one or more physical or logical controllers) controls some or all of the properties of the electroplating apparatus 900.

Signals for monitoring the process may be provided by analog and/or digital input connections of the system controller 930 from various process tool sensors. The signals for controlling the process may be output on the analog and digital output connections of the process tool. Non-limiting examples of process tool sensors that may be monitored include mass flow controllers, pressure sensors (such as manometers), thermocouples, optical position sensors, etc. Appropriately programmed feedback and control algorithms may be used with data from these sensors to maintain process conditions.

A hand-off tool 940 may select a substrate from a substrate cassette such as the cassette 942 or the cassette 944. The cassettes 942 or 944 may be front opening unified pods (FOUPs). A FOUP is an enclosure designed to hold substrates securely and safely in a controlled environment and to allow the substrates to be removed for processing or measurement by tools equipped with appropriate load ports and robotic handling systems. The hand-off tool 940 may hold the substrate using a vacuum attachment or some other attaching mechanism.

The hand-off tool 940 may interface with a wafer handling station 932, the cassettes 942 or 944, a transfer station 950, or an aligner 948. From the transfer station 950, a hand-off tool 946 may gain access to the substrate. The transfer station 950 may be a slot or a position from and to which hand-off tools 940 and 946 may pass substrates without going through the aligner 948. In some embodiments, however, to ensure that a substrate is properly aligned on the hand-off tool 946 for precision delivery to an electroplating module, the hand-off tool 946 may align the substrate with an aligner 948. The hand-off tool 946 may also deliver a substrate to one of the electroplating modules 902, 904, or 906 or to one of the three separate modules 912, 914, and 916 configured for various process operations.

An example of a process operation according to the methods described above may proceed as follows: (1) electrodeposit copper or another material onto a substrate in the electroplating module 904; (2) rinse and dry the substrate in SRD in module 912; and, (3) perform edge bevel removal in module 914.

An apparatus configured to allow efficient cycling of substrates through sequential plating, rinsing, drying, and PEM process operations may be useful for implementations for use in a manufacturing environment. To accomplish this, the module 912 can be configured as a spin rinse dryer and an edge bevel removal chamber. With such a module 912, the substrate would only need to be transported between the electroplating module 904 and the module 912 for the copper plating and EBR operations. In some embodiments the methods described herein will be implemented in a system which comprises an electroplating apparatus and a stepper.

Figure 10:
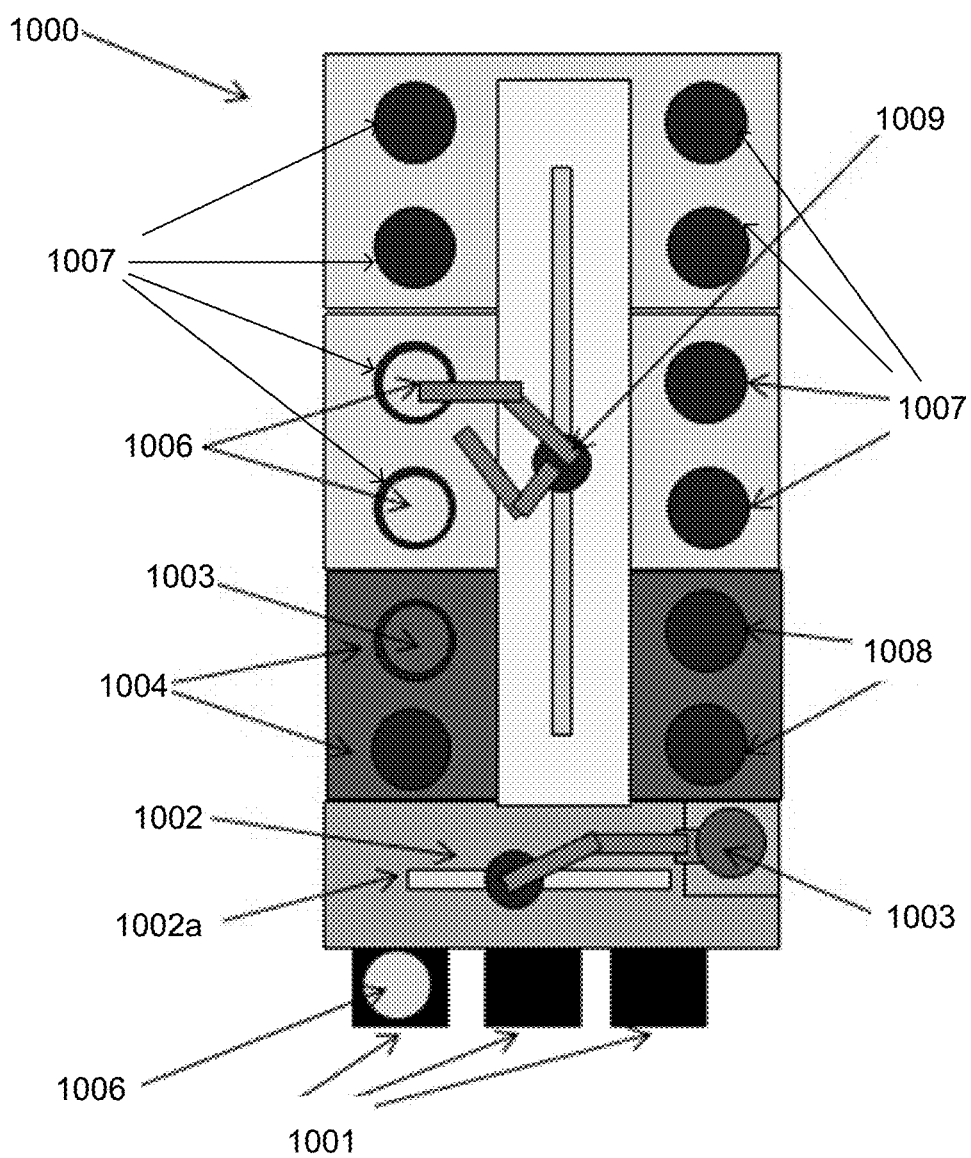

An alternative embodiment of an electrodeposition apparatus 1000 is schematically illustrated in FIG. 10. In this embodiment, the electrodeposition apparatus 1000 has a set of electroplating cells 1007, each containing an electroplating bath, in a paired or multiple "duet" configuration. In addition to electroplating per se, the electrodeposition apparatus 1000 may perform a variety of other electroplating related processes and sub-steps, such as spin-rinsing, spin-drying, metal and silicon wet etching, electroless deposition, pre-wetting and pre-chemical treating, reducing, annealing, photoresist stripping, and surface pre-activation, for example. The electrodeposition apparatus 1000 is shown schematically looking top down in FIG. 10, and only a single level or "floor" is revealed in the figure, but it is to be readily understood by one having ordinary skill in the art that such an apparatus, e.g., the Novellus Sabre™ 3D tool, can have two or more levels "stacked" on top of each other, each potentially having identical or different types of processing stations.

Referring once again to FIG. 10, the substrates 1006 that are to be electroplated are generally fed to the electrodeposition apparatus 1000 through a front end loading FOUP 1001 and, in this example, are brought from the FOUP to the main substrate processing area of the electrodeposition apparatus 1000 via a front-end robot 1002 that can retract and move a substrate 1006 driven by a spindle 1003 in multiple dimensions from one station to another of the accessible stations—two front-end accessible stations 1004 and also two front-end accessible stations 1008 are shown in this example. The front-end accessible stations 1004 and 1008 may include, for example, pre-treatment stations, and spin rinse drying (SRD) stations. Lateral movement from side-to-side of the front-end robot 1002 is accomplished utilizing robot track 1002*a*. Each of the substrates 1006 may be held by a cup/cone assembly (not shown) driven by a spindle 1003 connected to a motor (not shown), and the motor may be attached to a mounting bracket 1009. Also shown in this example are the four "duets" of electroplating cells 1007, for a total of eight electroplating cells 1007. A system controller (not shown) may be coupled to the electrodeposition apparatus 1000 to control some or all of the properties of the electrodeposition apparatus 1000. The system controller may be programmed or otherwise configured to execute instructions according to processes described earlier herein.

System Controller

In some implementations, a controller is part of a system, which may be part of the above-described examples. Such systems can comprise semiconductor processing equipment, including a processing tool or tools, chamber or chambers, a platform or platforms for processing, and/or specific processing components (a wafer pedestal, a gas flow system, etc.). These systems may be integrated with electronics for controlling their operation before, during, and after processing of a semiconductor wafer or substrate. The electronics may be referred to as the "controller," which may control various components or subparts of the system or systems. The controller, depending on the processing requirements and/or the type of system, may be programmed to control any of the processes disclosed herein, including the delivery of processing gases, temperature settings (e.g., heating and/or cooling), pressure settings, vacuum settings, power settings, radio frequency (RF) generator settings, RF matching circuit settings, frequency settings, flow rate settings, fluid delivery settings, positional and operation settings, wafer transfers into and out of a tool and other transfer tools and/or load locks connected to or interfaced with a specific system. In a particular example, the system controller controls the position of the substrate holder. The system controller may instruct the lift mechanism to position the substrate holder at a plating position, a cleaning position, a drying position, and/or a detection position, as appropriate. The system controller may also instruct the plating sensor to take measurements as needed to perform the methods described herein. The system controller may also instruct the apparatus to dry the sensor target area prior to taking a measurement with the plating sensor, and/or to re-wet the sensor target area after taking a measurement with the plating sensor and prior to processing a new wafer.

Broadly speaking, the controller may be defined as electronics having various integrated circuits, logic, memory, and/or software that receive instructions, issue instructions, control operation, enable cleaning operations, enable endpoint measurements, and the like. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process on or for a semiconductor wafer or to a system. The operational parameters may, in some embodiments, be part of a recipe defined by process engineers to accomplish one or more processing steps during the fabrication of one or more layers, materials, metals, oxides, silicon, silicon dioxide, surfaces, circuits, and/or dies of a wafer.

The controller, in some implementations, may be a part of or coupled to a computer that is integrated with, coupled to the system, otherwise networked to the system, or a combination thereof. For example, the controller may be in the "cloud" or all or a part of a fab host computer system, which can allow for remote access of the wafer processing. The computer may enable remote access to the system to monitor current progress of fabrication operations, examine a history of past fabrication operations, examine trends or performance metrics from a plurality of fabrication operations, to change parameters of current processing, to set processing steps to follow a current processing, or to start a new process. In some examples, a remote computer (e.g. a server) can provide process recipes to a system over a network, which may include a local network or the Internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits on a chamber in communication with one or more integrated circuits located remotely (such as at the platform level or as part of a remote computer) that combine to control a process on the chamber.

Without limitation, example systems may include a plasma etch chamber or module, a deposition chamber or module, a spin-rinse chamber or module, a metal plating chamber or module, a clean chamber or module, a bevel edge etch chamber or module, a physical vapor deposition (PVD) chamber or module, a chemical vapor deposition (CVD) chamber or module, an atomic layer deposition (ALD) chamber or module, an atomic layer etch (ALE) chamber or module, an ion implantation chamber or module, a track chamber or module, and any other semiconductor processing systems that may be associated or used in the fabrication and/or manufacturing of semiconductor wafers.

As noted above, depending on the process step or steps to be performed by the tool, the controller might communicate with one or more of other tool circuits or modules, other tool components, cluster tools, other tool interfaces, adjacent tools, neighboring tools, tools located throughout a factory, a main computer, another controller, or tools used in material transport that bring containers of wafers to and from tool locations and/or load ports in a semiconductor manufacturing factory.

The various hardware and method embodiments described above may be used in conjunction with lithographic patterning tools or processes, for example, for the fabrication or manufacture of semiconductor devices, displays, LEDs, photovoltaic panels and the like. Typically, though not necessarily, such tools/processes will be used or conducted together in a common fabrication facility.

Lithographic patterning of a film typically comprises some or all of the following steps, each step enabled with a number of possible tools: (1) application of photoresist on a workpiece, e.g., a substrate having a silicon nitride film formed thereon, using a spin-on or spray-on tool; (2) curing of photoresist using a hot plate or furnace or other suitable curing tool; (3) exposing the photoresist to visible or UV or x-ray light with a tool such as a wafer stepper; (4) developing the resist so as to selectively remove resist and thereby pattern it using a tool such as a wet bench or a spray developer; (5) transferring the resist pattern into an underlying film or workpiece by using a dry or plasma-assisted etching tool; and (6) removing the resist using a tool such as an RF or microwave plasma resist stripper. In some embodiments, an ashable hard mask layer (such as an amorphous carbon layer) and another suitable hard mask (such as an antireflective layer) may be deposited prior to applying the photoresist.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above described processes may be changed. Certain references have been incorporated by reference herein. It is understood that any disclaimers or disavowals made in such references do not necessarily apply to the embodiments described herein. Similarly, any features described as necessary in such references may be omitted in the embodiments herein.

The subject matter of the present disclosure includes all novel and nonobvious combinations and sub-combinations of the various processes, systems and configurations, and other features, functions, acts, and/or properties disclosed herein, as well as any and all equivalents thereof.

What is claimed is:

1. An electroplating apparatus comprising:
    an electrolyte vessel configured to hold electrolyte during electroplating;
    a substrate holder configured to support a substrate during electroplating, wherein the substrate holder is annularly shaped and supports the substrate at its periphery, the substrate holder comprising a sensor target area;
    a plating sensor comprising a light source aimed at the sensor target area, wherein the plating sensor distinguishes between (i) areas on the sensor target area where unwanted metal deposits are present and (ii) areas on the sensor target area where unwanted metal deposits are absent;
    an alignment fixture that fits over the substrate holder, the alignment fixture comprising a first portion and a second portion, wherein the first and second portions are distinguishable from one another with respect to a property measured by the plating sensor.

2. The electroplating apparatus of claim 1, wherein the substrate holder comprises a cup and a lip seal, the cup comprising a bottom surface and an inner wall, wherein the lip seal is positioned at the top of the inner wall of the cup.

3. The electroplating apparatus of claim 2, wherein the sensor target area is on the lip seal.

4. The electroplating apparatus of claim 2, wherein the sensor target area is on the inner wall of the cup.

5. The electroplating apparatus of claim 4, wherein the sensor target area is on both the inner wall of the cup and the lip seal.

6. The electroplating apparatus of claim 1, further comprising a drip shield, wherein the plating sensor is positioned on the drip shield.

7. The electroplating apparatus of claim 6, wherein the drip shield comprises a wall and a central opening through which the substrate holder fits.

8. The electroplating apparatus of claim 1, wherein the plating sensor is a color-based sensor, an intensity-based sensor, or a camera.

9. The electroplating apparatus of claim 1, wherein the substrate holder comprises a cup and a lip seal, the cup comprising a bottom surface and an inner wall, wherein the lip seal is positioned at the top of the inner wall of the cup, wherein the first portion of the alignment fixture is proximate the lip seal such that the plating sensor detects the presence or absence of metal deposits on the lip seal.

10. The electroplating apparatus of claim 1, wherein the substrate holder comprises a cup and a lip seal, the cup comprising a bottom surface and an inner wall, wherein the lip seal is positioned at the top of the inner wall of the cup, wherein the first portion of the alignment fixture is proximate the inner wall of the cup such that the plating sensor detects the presence or absence of metal deposits on the inner wall of the cup.

11. The electroplating apparatus of claim 1, further comprising a dryer that dries the sensor target area.

12. The electroplating apparatus of claim 11, further comprising a controller having executable instructions to dry the sensor target area prior to detecting the presence or absence of unwanted metal deposits using the plating sensor.

13. The electroplating apparatus of claim 1, wherein the substrate holder is rotatable with respect to the plating sensor.

14. The electroplating apparatus of claim 1, further comprising an inlet configured to deliver fluid to the sensor target area.

15. The electroplating apparatus of claim 14, further comprising a controller having executable instructions to wet the sensor target area with fluid after the plating sensor is used to detect the presence or absence of unwanted metal deposits in the sensor target area and before the electroplating apparatus is used to electroplate on a new substrate.

16. A method of detecting the presence or absence of an unwanted metal deposit on a substrate holder of an electroplating apparatus, the method comprising:
    positioning the substrate holder at a detection position, the substrate holder comprising a sensor target area;
    aligning a plating sensor and the sensor target area using an alignment fixture that fits over the substrate holder, the alignment fixture comprising a first portion and a second portion, wherein the first and second portions are distinguishable from one another with respect to a property measured by the plating sensor; and
    operating the plating sensor comprising a light source to detect the presence or absence of the unwanted metal deposit in the sensor target area, wherein the plating sensor and the sensor target area are positioned on opposite sides of the electroplating apparatus such that a line of sight of the plating sensor extends across the electroplating apparatus.

* * * * *